(12) United States Patent
Florescu

(10) Patent No.: US 9,244,068 B2
(45) Date of Patent: *Jan. 26, 2016

(54) FILTRATION DEVICE FOR ASSAYS

(71) Applicant: Silicon BioDevices, Inc., Palo Alto, CA (US)

(72) Inventor: Octavian Florescu, Berkeley, CA (US)

(73) Assignee: Silicon BioDevices, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/523,759

(22) Filed: Oct. 24, 2014

(65) Prior Publication Data

US 2015/0044097 A1 Feb. 12, 2015

Related U.S. Application Data

(63) Continuation of application No. 13/471,227, which is a continuation of application No. PCT/US2010/002994, filed on Nov. 16, 2010, now Pat. No. 8,895,320.

(60) Provisional application No. 61/261,726, filed on Nov. 16, 2009.

(51) Int. Cl.
*B01L 3/00* (2006.01)
*G01N 33/543* (2006.01)

(52) U.S. Cl.
CPC .... *G01N 33/54386* (2013.01); *B01L 3/502753* (2013.01); *G01N 33/54326* (2013.01); *B01L 2200/0647* (2013.01); *B01L 2200/12* (2013.01); *B01L 2300/0636* (2013.01); *B01L 2300/0681* (2013.01); *B01L 2300/0874* (2013.01); *B01L 2400/043* (2013.01); *G01N 2458/00* (2013.01); *Y10T 137/8013* (2015.04); *Y10T 436/25375* (2015.01)

(58) Field of Classification Search
None
See application file for complete search history.

(56) References Cited

U.S. PATENT DOCUMENTS

| 5,208,163 | A | 5/1993 | Charlton et al. |
| 5,723,345 | A | 3/1998 | Yamauchi et al. |
| 5,736,188 | A | 4/1998 | Alcock et al. |
| 5,827,681 | A | 10/1998 | Krug et al. |
| 6,743,399 | B1 | 6/2004 | Weigl et al. |
| 2002/0119470 | A1 | 8/2002 | Nerenberg et al. |

(Continued)

FOREIGN PATENT DOCUMENTS

| JP | 2005-00988 | 1/2005 |
| WO | WO 03/034026 | 4/2003 |

(Continued)

OTHER PUBLICATIONS

Thorslund, S. et al. "Bioactive heparin immobilized onto microfluidic channels in poly(dimethylsiloxane) results in hydrophilic surface properties," *Colloids and Surface: B. BioInterfaces*, vol. 46, No. 4, pp. 240-247.

*Primary Examiner* — Melanie Y Brown
*Assistant Examiner* — Rebecca Martinez
(74) *Attorney, Agent, or Firm* — Levine Bagade Han LLP

(57) ABSTRACT

A device and method for filtering blood is disclosed herein. The device can filter blood and attach analytes within the blood to magnetic particles. The analytes can then be strongly bound to an analyzing device by a magnetic force. The analytes can then be counted by the analyzing device and the result can be displayed.

6 Claims, 16 Drawing Sheets

(56) References Cited

U.S. PATENT DOCUMENTS

| | | |
|---|---|---|
| 2003/0148542 A1 | 8/2003 | Pawlak et al. |
| 2003/0185713 A1 | 10/2003 | Leonard et al. |
| 2005/0112023 A1 | 5/2005 | Liang |
| 2007/0031283 A1 | 2/2007 | Davis et al. |
| 2008/0153096 A1 | 6/2008 | Witty et al. |
| 2009/0060357 A1 | 5/2009 | Neijzen |
| 2009/0091926 A1 | 7/2009 | Florescu et al. |
| 2009/0269767 A1 | 10/2009 | Soderlund et al. |
| 2012/0258466 A1 | 10/2012 | Florescu |

FOREIGN PATENT DOCUMENTS

| | | |
|---|---|---|
| WO | WO 2007/002579 | 1/2007 |
| WO | WO 2008/055257 | 5/2008 |
| WO | WO 2009/013683 | 1/2009 |
| WO | WO 2009/044088 | 4/2009 |
| WO | WO 2009/060357 | 5/2009 |
| WO | WO 2009/068584 | 6/2009 |
| WO | WO 2009/091926 | 7/2009 |
| WO | WO 2009/112982 | 9/2009 |
| WO | WO 2010/086772 | 8/2010 |
| WO | WO 2010/119380 | 10/2010 |
| WO | WO 2011/027262 | 3/2011 |
| WO | WO 2011/059512 | 5/2011 |

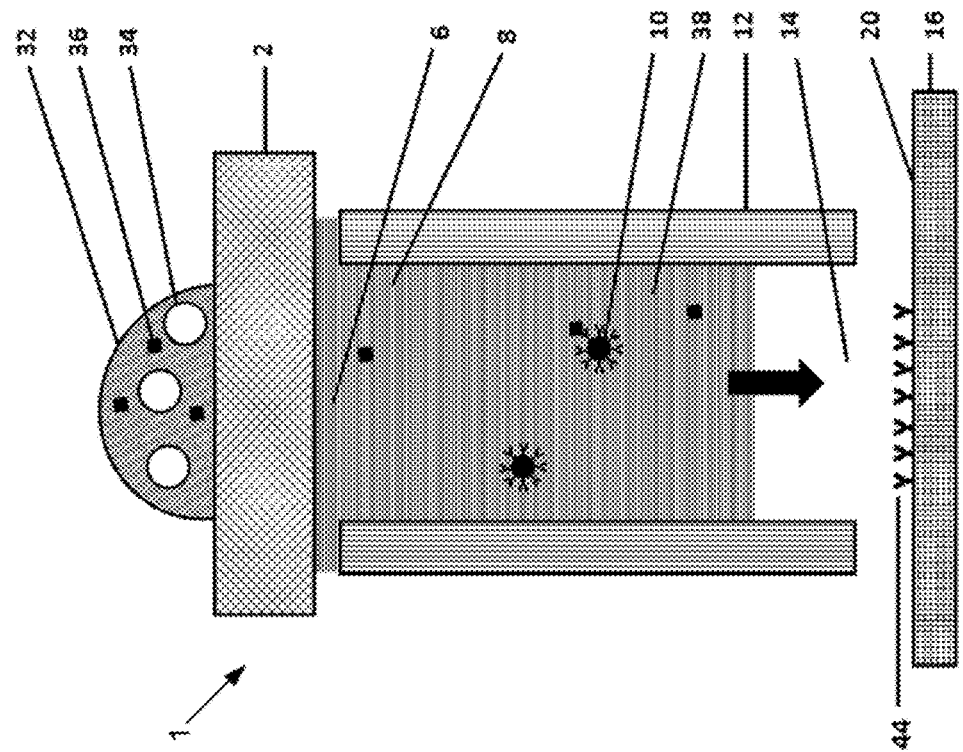
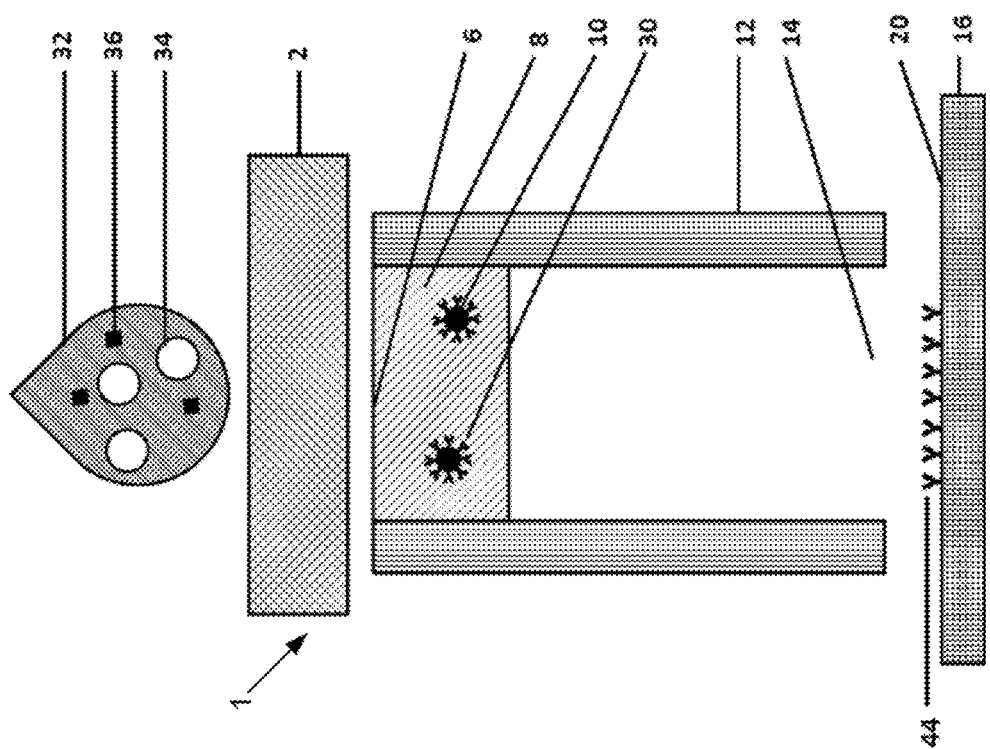

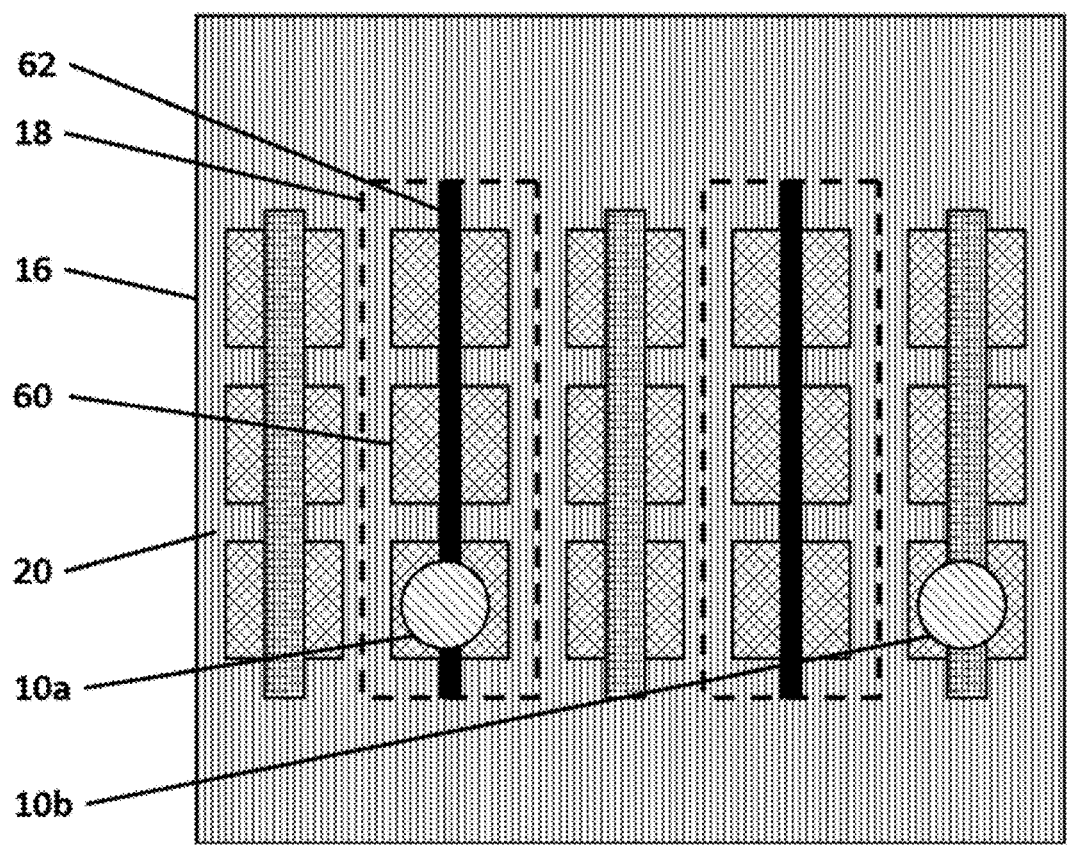
Fig.
12

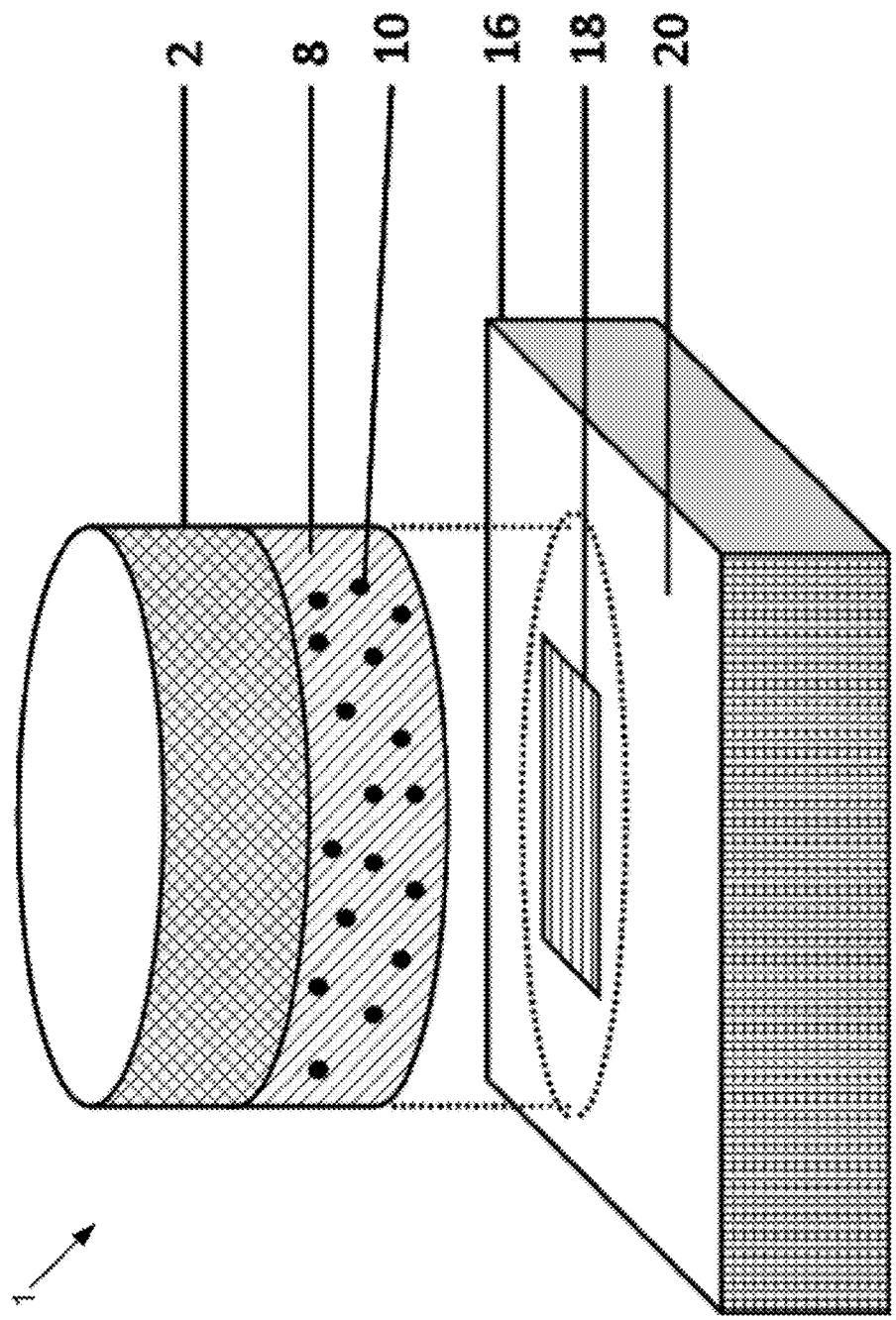

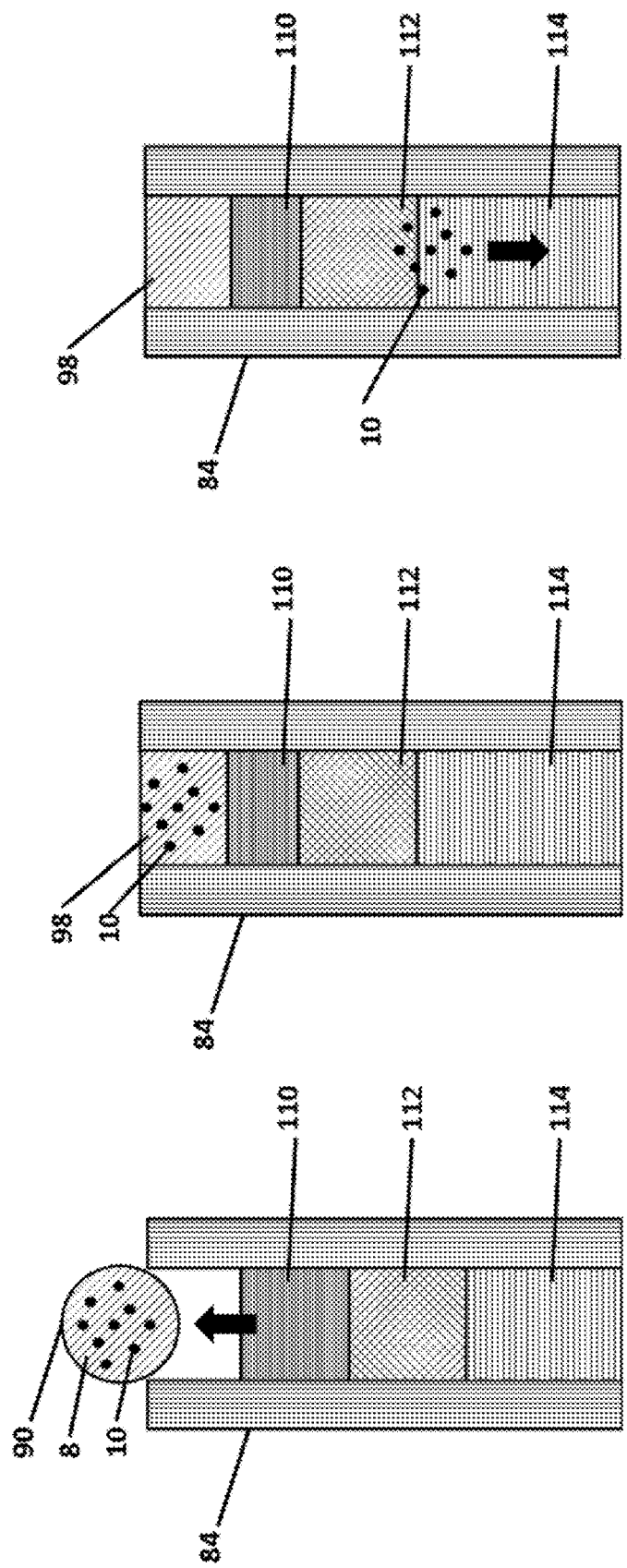

FILTRATION DEVICE FOR ASSAYS

CROSS-REFERENCE TO RELATED APPLICATIONS

The present application is a continuation of U.S. patent application Ser. No. 13/471,227, filed May 14, 2012, which is a continuation of PCT International Application No. PCT/US2010/002994, filed Nov. 16, 2010, which claims the benefit of U.S. Provisional Application No. 61/261,726, filed Nov. 16, 2009, all of which are incorporated herein by reference in their entireties.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

A device and method for use in the field of chemical testing is disclosed. More particularly, the device can be used for filtering whole blood for testing on an integrated circuit.

2. Summary of the Related Art

Point-of-Care (POC) diagnostic medical devices facilitate early stage detection of diseases, enable more individually tailored therapies, and allow doctors to follow up with patients more easily to see if prescribed treatments are working. To ensure widespread adoption, these tools must be accurate, easy to use by untrained individuals, and inexpensive to produce and distribute. Immuno-Assay (IA) applications are particularly well-suited for the POC since a wide range of conditions, from cardiovascular disease to cancer to communicable infections, can be identified from soluble protein bio-markers. The detection and quantitation of these bio-markers from raw samples such as whole blood often involves labeling the target protein using fluorescent or phosphorescent molecules, enzymes, quantum dots, metal particles or magnetic particles. For high sensitivity applications, the labels specifically bound to the target analytes must be distinguished from the unbound ones that contribute to background noise. By combining both label separation and detection in a low cost, easy to use format, the Immuno-Chromatographic Test (ICT) achieves stand-alone operation, i.e. the ability to perform an assay without necessitating a secondary device like an electronic reader or an external sample preparation system. Stand-alone operation is an often overlooked attribute, but one that is key to the popularity of ICTs, achieved despite other drawbacks such as low biochemical sensitivity, user interpretation, inaccurate quantitation, timing requirements, and awkward multiplexing.

The use of magnetic particle labeling is ideal for POC applications; magnetic particles can be individually detected, so sub-pico molar sensitivities can be achieved without signal amplification steps that can take up to an hour as in case of enzymatic labeling. Also, by micro-arraying the sensor areas onto which the particles bind, multiplexed operation can be achieved at low cost. The use of magnetic particles can reduce incubation times, since they can bind to the target analytes with solution-phase kinetics due to their high surface area to volume ratio. Furthermore, the ability to pull the magnetic particles out of solution magnetically and gravitationally overcomes the slow diffusion processes that plague most high sensitivity protocols. The signals from magnetic particles can be stable over time, insensitive to changes in temperature or chemistries and detected in opaque or translucent solutions like whole blood or plasma. The biological magnetic background signal can be low, so high assay sensitivity can be achieved with minimal sample preparation. Most importantly, the use of magnetic particles as assay labels can permit stand-alone device operation, since these particles can be both manipulated and detected electromagnetically.

"Magnetic particles" are typically nano-meter or micro-meter sized particles that display magnetic, diamagnetic, ferromagnetic, ferrimagnetic, paramagnetic, super-paramagnetic or antiferromagnetic behavior. "Magnetic particles" can refer to individual particles or larger aggregates of particles such as magnetic beads.

ICTs in which magnetic particles are used as the assay labels are an improvement to conventional ICTs since the detection of the particles is not limited to the surface of the strip, but can be performed throughout the volume of the strip, resulting in higher sensitivities and improved quantitative accuracy. However, volumetric detection of magnetic particles cannot be readily integrated in a stand-alone device, so these implementations require an external device to measure the volume magnetization in the strip.

One alternative for integration into a stand-alone device is to use magnetic particles that bind to the target analytes in solution before sedimenting via gravity or magnetic force to sensor areas where the specifically bound particles can be detected. A bio-functionalized IC can be used to detect the specifically bound particles. However, most IC-based immuno-assay implementations reported to date cannot operate stand-alone since they require either off-chip components for particle detection, or micro-fluidic actuation for particle manipulation and sample preparation. Other implementations simply cannot reach the cost structures necessary to compete in the current marketplace.

For POC application, it is desirable that the sample preparation be rapid since the assay is limited to 10-15 minutes. In addition, to obviate the need for refrigeration equipment and to facilitate storage and distribution, a dry sample preparation system is desired. It is also desirable to have a sample preparation system that receives small unprocessed samples from patients. The average hanging drop of blood from a finger stick yields approximately 15 µl of fluid. For more fluid, a complicated venu-puncture can be necessary. Moreover, the sample preparation system must be low-cost since biological contamination concerns dictate that all material in contact with biological samples be discarded. It is also desirable that the sample preparation system be amenable to multiplexed operation.

BRIEF SUMMARY OF THE INVENTION

A sample preparation system that can fulfill the requirements for speed, cost, and performance described above is disclosed.

A porous material like a membrane filter can obviate the need for centrifugation or complicated micro-fluidic sample preparation. Since the membrane filters are compact and inexpensive, system cost can be reduced, enabling stand-alone POC operation. The membranes can separate the plasma from the whole blood cells without additional support in under 30 seconds. Incubation of the filtrate with functionalized magnetic particles can achieve solution phase kinetics for rapid operation with sub pico-molar sensitivities. The system can use an IC to perform the detection of the magnetic particles, for example to enable low cost, stand-alone operation. The system can have a combination of a filter, capillary, magnetic particles and an IC, for example resulting in a stand-alone, accurate, multiplexed platform with the form factor of a thumb-drive. The size of the entire system excluding a battery and display can be under about 1 cm$^3$.

The device can be used for immuno-assays. The device can be used for nucleic acid, small molecule and inorganic molecule testing, or combinations thereof.

A sample preparation system comprising a membrane filter and a capillary channel configured to deliver magnetic particles to the exposed surface of an integrated circuit (IC) that manipulates and detects the particles is disclosed. The membrane filter can be placed horizontally, parallel to the surface of the IC, above the inlet to a capillary channel. The IC can be placed horizontally with one or more exposed sensor areas below the outlet of the capillary channel. Chemically functionalized magnetic particles and other reagents can be stored in a dried state in the membrane filter, the capillary, the sensor areas on the surface of the IC, or combinations thereof. The magnetic particles can be dried and stored at the inlet of the capillary channel. An aqueous biological sample, such as whole blood, containing one or more target analytes can be deposited on the top of the membrane filter. The large particulate matter in the sample, such as whole blood cells, can be trapped on top or in the membrane, while the filtrate containing the target analytes traverses the membrane into the inlet of the capillary, where the magnetic particles can re-suspend and bind to the target analytes in the filtrate. The filtrate with the re-suspended magnetic particles can flow through the capillary and onto the sensor areas on the surface of the IC as a result of capillary action.

Magnetic particles bound to a target analyte can bind strongly through specific chemical interactions to the functionalized sensor areas on the surface of the IC. The number of magnetic particles specifically bound to the surface of the IC is representative of the concentration of the target analyte in the biological sample presented.

The surface of the IC can contain one or more sensor areas, defined as the areas on the surface of the IC in which the specifically bound magnetic particles lie. The sensor areas correspond to the area on the surface of the chip in which magnetic particle sensors can detect specifically bound magnetic particles. The magnetic particle sensors can be embedded in the IC. Magnetic particle sensors can be placed outside of the sensor areas to detect the non-specifically bound magnetic beads removed from the sensor areas for an accurate count of the total number of magnetic particles.

The IC can contain one or more magnetic force generators to manipulate the non-specifically bound magnetic particles on the sensor areas. These magnetic forces can be used to attract the magnetic beads to the sensor areas and to remove the non-specifically bound magnetic particles from the sensor areas. The system can have two or more capillaries, for example where the inlet of a delivery capillary is placed directly below the filter and delivers the filtrate into a sedimentation capillary which is placed vertically directly above the sensor area. The dried magnetic particles can be placed at the top of the sedimentation capillary. From the top of the sedimentary capillary, the dried magnetic particles can sediment to the sensor area once the filtrate reaches them. The length of time of the assay can be determined by the height of the sedimentation capillary.

The system can have multiple unconnected capillaries below multiple unconnected membranes to deliver distinct filtrates to multiple unconnected sensor areas on the sensor areas of one or more distinct ICs for multiplexed operation.

The system can have a membrane filter or one or more membrane filter assemblies comprising multiple stacked membrane filters of the same or varying characteristics, where each filter can be loaded with different dried proteins, reagents, chemicals, magnetic particles and combinations thereof.

The device may be configured to take whole or previously filtered blood, urine, tear, sputum, fecal, oral, nasal samples or other biological or non-biological aqueous samples.

The characteristics of the membrane can be varied to accommodate the different sample types. The membrane filter can be replaced or used in conjunction with a porous material like a glass fiber or a nitro-cellulose strip.

Chemicals, such as, but not limited to: aptamers, oligo-nucleotides, proteins, agents to prevent clotting, target analytes for internal calibration curves, bindive catalytic agents, magnetic particles, or combinations thereof may be dried in the membrane filter assembly along the shaft of the capillary or on the surface of the IC and can be re-solubilized by the blood plasma but remain bound to the surface upon which they were dried.

BRIEF DESCRIPTION OF THE DRAWINGS

FIGS. 4 through 7 are side cross-sectional views of a variation of a method of using the system.

FIG. 12 is a top view of a variation of a method for using a variation of the integrated circuit.

FIGS. 13 through 18 are perspective, exploded and partially see-through views of variations of the system.

FIGS. 23 through 25 are partial cross-sectional views of a variation of a method for incubating the magnetic particles with different fluids.

DETAILED DESCRIPTION

Figure 1:
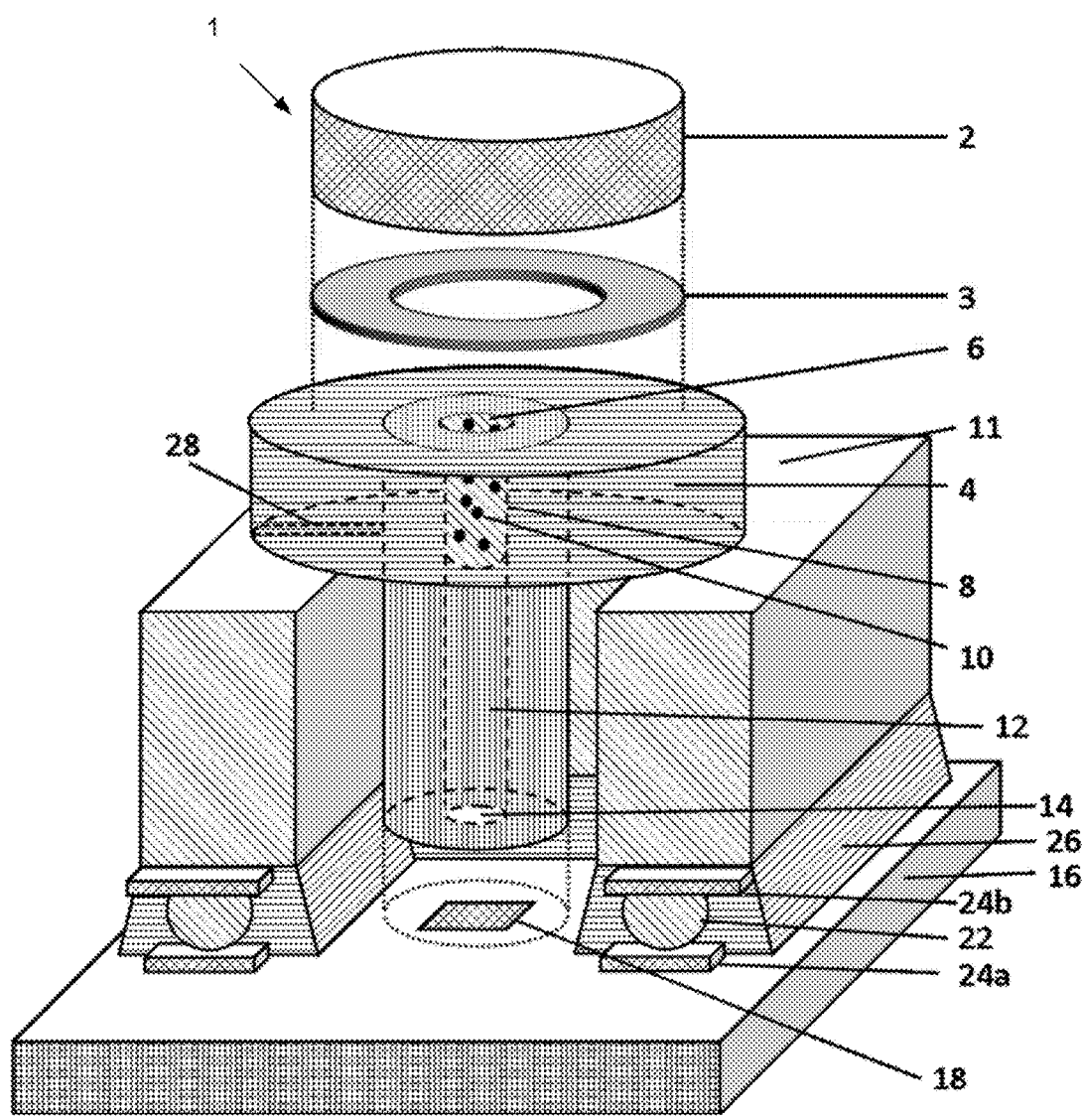
FIGS. 1 and 2 are a perspective exploded and partially see-through view, and a cross-sectional view, respectively, of a variation of the system.

A blood filtration device or system 1 for magnetic particle-labeled chemical assays, system components and mechanisms thereof are described in FIGS. 1-14.

The system 1 can have a filter support structure 4 mounted on the top surface of a printed circuit board 11 directly above an opening 29 formed in the printed circuit board by drilling, punching, molding, or other suitable methods. The filter support structure 4 may have tabs or other features to maintain alignment with the printed circuit board opening 29. The filter support structure 4 may be fabricated from any rigid material, such as injection molded plastic. The filter support structure 4 may be attached to the printed circuit board 11 by an adhesive or by press-fitting. A ventilation channel 28 can be formed by a radial groove in the bottom surface of the filter support structure 4 and/or the top surface of printed circuit board 11.

Printed circuit board 11 can be fabricated from rigid materials such as fiberglass laminate, or from flexible materials laminated to a rigid substrate, such as polyimide film laminated to a plastic substrate.

An integrated circuit 16 can be attached to the bottom side of printed circuit board 11 for example by a plurality of solder bumps 22. Solder bumps 22 can be attached to IC bond pads 24a and printed circuit board metallization 24b, thus providing mechanical attachment and electrical interconnection between the integrated circuit 16 and the printed circuit board 11. A polymer seal 26 can be placed between the integrated circuit 16 and the printed circuit board 11, forming a sealed cavity and protecting the electrical connections from contamination by fluids. Other methods of attachment, sealing, and electrical interconnection may also be used. For example, electrical connections may be made using bond wires, spring contacts, conductive polymers, or combinations thereof; mechanical attachment may be provided by adhesives, clips, or other suitable methods; sealing may be provided by insulating coatings, hydrophobic coatings, flexible seals, or combinations thereof.

A membrane filter 2 can be attached to the top of a filter support structure 4 using an adhesive ring 3. The membrane filter 2 can be composed of but not limited to polyvinylpyrrolidone/polyethersulfone (PVP/PES). The membrane filter 2 can have a porosity gradient to effectively trap cells in whole blood while allowing blood plasma and the analytes therein to pass through the membrane. The optimal filter can be a 0.26 mm thick PVP/PES filter with about a 35 μm pore size on the top and about a 2.5 μm pore size on the bottom. The membrane filter 2 can be cut into a disc having a membrane filter diameter 150 can be from about 0.5 mm to about 30 mm, more narrowly from about 2 mm to about 20 mm, yet more narrowly from about 1 mm to about 8 mm, for example about 4 mm. The membrane filter 2 can be oriented in a horizontal plane. The membrane filter 2 can be oriented in a plane parallel with the top surface 20 of the IC 16 and/or the sensor areas 18 of the IC 16. The membrane filter 2 can be oriented parallel with the top surface of the filter support structure 4.

The adhesive ring 3 may be formed out of any liquid-resistant adhesive material, such as double sided adhesive tape or a liquid adhesive. The membrane filter 2 can also be attached to filter support structure 4 by any other suitable means, for example using epoxy or other adhesive, welding, melting, snap-fitting, or combinations thereof.

A capillary channel 12 can be attached to the filter support structure 4, such that a capillary inlet 6 can be positioned directly below filter 2, and a capillary outlet 14 can be positioned directly above sensor areas 18 on the surface 20 of the integrated circuit 16. The capillary outlet 14 can be positioned for example about 0.1 mm to about 1 mm away from the surface 20 of the integrated circuit 16. The capillary channel 12 may be integral with the filter support structure 4, or a separate unit attached to filter support structure 4 by suitable adhesives or a friction fit. The capillary channel 12 can have a capillary length 154 as stated elsewhere herein or from about 0.5 mm to about 10 cm, more narrowly from about 1 mm to about 5 mm, for example about 0.5 mm or about 10 cm. The capillary channel 12 can have a capillary inner diameter 156 as stated elsewhere herein or, for example, from about 0.25 mm to about 5 mm, more narrowly from about 0.25 mm to about 2.5 mm, for example about 0.25 mm or 5 mm. The capillary can receive about a 15 μl sample of whole blood obtained using a finger lancet. A capillary with a smaller capillary length 154 and inner diameter 156 can be selected for faster flow through the capillary 12. A capillary with a larger capillary length 154 and inner diameter 156 can be selected for slower flow through the capillary.

The capillary channel 12 can partially contact the surface 20 of the IC 16. A vent at the outlet 14 of the capillary opening can be provided to allow air to exit. The air pressure can be unvented to prevent or minimize the filtrate 38 from flowing onto the sensor areas 18.

A plurality of magnetic particles 10 and a bulking agent 8 can be lyophilized into a dry microsphere 90 having a microsphere diameter 160 for example, from about 0.1 mm to about 5 mm, more narrowly from about 1 mm to about 5 mm, yet more narrowly from about 0.5 mm to about 4 mm, for example about 2 mm.

The magnetic particles 10 can be dried in a microsphere 90 by lyophilization. The microsphere 90 can contain the magnetic particles 10 coated with antibodies 30 in PBS solution with about 0.05% Polyoxyethylene (20) sorbitan monolaurate (i.e., Polysorbate 20, Tween-20), and a bulking agent 8. The bulking agent 8 can be a sugar, a polymer, such as trehalose and/or poly(ethylene glycol), or combinations thereof. The poly(ethylene glycol) can be used with a molecular weight of about 4-8 kDa. The bulking agent can be over about 90% of the mass of the microsphere 90.

The microsphere 90 can be made by preparing a liquid solution of the appropriate amount (a variation for how this can be determined is explained below) of magnetic particles 10 and any other minor component plus about 10%-70% by weight of the bulking agent 90. The liquid solution can be dispensed into liquid nitrogen. The dispensed solution can flash freeze in about a minute or less, producing frozen microsphere 90. The frozen microsphere 90 can be transferred to a container that can be placed in a lyophilizer. The microsphere 90 can then be lyophilized according to a programmed temperature profile designed to ensure that they do not melt (i.e., "meltback") during the process. The meltback can occur as the amount of water (e.g., ice) decreases while the amount of solid solute remains constant. Changing the ratio of solute to water can lower the freezing point of the microspheres. If the lyophilizer is not cold enough, meltback can occur. However, too low a lyophilizer temperature can increase the time required to dry the microspheres.

As an example, a possible production process is described;
a. A microsphere 90 of about 7.5 μl volume can be dispensed using a precision pump into liquid nitrogen.
b. The microsphere with additional liquid nitrogen can be transferred to metal or Pyrex containers and placed onto a pre-chilled tray on the lyophilizer. The tray temperature can be set to about −30° C.
c. The condenser can be turned on the lyophilizer and the primary drying phase begun. The vacuum can be generally about 50±10 mtorr in the chamber.
d. This primary drying phase can be at least about 16 hours long.
e. The shelf temperature can be raised to about −10° C. and can be held for at least about 4 hours.
f. The shelf temperature can be raised to about +25° C. and held for about 15 minutes before removing the particles and placing them in two separate vials.
g. The particles can be inspected for debris, uniformity and melting.
h. The dried products can be kept desiccated.

Very little magnetic particle 10 clustering can be produced.

Once dry, the microsphere 90 can be protected from moisture. The volume of the dried microsphere, as defined by the outer perimeter of the sphere, can include about 90% void. The microsphere 90 can have a very large effective surface area and can be very hydrophilic. In the presence of liquid water, the microsphere 90 can dissolve very quickly. Since the whole three dimensional structure of the microsphere 90 can collapse all at once, the magnetic particles 10 contained in the microsphere 90 can be mixed with the water and be re-suspended upon collapse of the microsphere 90 without clustering. The volume of the liquid that dissolves the microsphere 90 can be controlled, and the concentration of all components in the solution resulting from the re-hydration of the microsphere 90 can be calculated. There can be approximately 1,000,000 magnetic particles 10 in each about 7.5 µl microsphere 90.

The microsphere 90 can be press-fit into the capillary inlet 6, where the microsphere 90 can be immobilized. Since the microsphere 90 diameter can be larger than the inner diameter of the capillary channel 12, the microsphere 90 can be deformed into a cylindrical shape upon insertion into the capillary. The capillary inlet 6 can be tapered, for example, to accept the entire microsphere 90 without requiring the microsphere 90 to be deformed. The microsphere 90 can be made large enough such that the microsphere 90 cannot travel past the capillary inlet 6 or the length of the capillary channel adjacent to the capillary inlet 6 and further into the capillary channel 12.

The reagents can be, but need not be dried or lyophilized in the form of a microsphere 90. The reagents can be dried or lyophilized into different shapes that can be packed into the capillary channel 12.

Chemicals to improve the performance of the assay can be lyophilized along with the magnetic particles 10 in the microspheres 90. For example, these can include buffer salts, pH adjusters, non-specific binding blockers, anionic, cationic, non-ionic and zwitterionic detergents, anti-foam agents, inorganic salts, chelators, heterophilic antibody blockers, protein stabilizers, anti-microbial agents and anti-agglutination agents. In addition or separately, sets of reagents such as surface antibodies 44 for binding to the magnetic particles 10 in the presence of the target analyte 36 or blocking agents can be bound and dried on the sensor areas 18 on the surface 20 of the IC 16.

The filtration sub-system can have the support structure 4, the membrane filter 2, the capillary 12 and the dried magnetic particles 10. The filtration sub-system can be manufactured independently of the electronic sub-system consisting of the integrated circuit 16 and the PCB 11. The IC 16 can be manufactured, tested and bio-functionalized inexpensively before integration into the broader system.

To functionalize the IC 16, the sensor areas 18 can be coated with one or more chemicals such as but not limited to antibodies 44, oligonucleotides and aptamers that bind specifically to the target analyte 36. To reduce non-specific binding of magnetic particles 10 to the sensor areas 18, is the sensor area 18 can be coated with blocking chemical such as but not limited to albumin, casein and non-fat dried milk. Once coated and blocked the sensor areas 18 can be dried and the electronic sub-system can be combined with the filtration sub-system.

In a sandwich capture immuno-assay format, the magnetic particles 10 can be covalently conjugated to antibodies 30 specific to an epitope on a target analyte 36 in the blood sample 32 presented. The sensor areas 18 can be coated with a second antibody 44 specific to a second epitope on the same target analyte 36. For multiplexed operation, the sensor areas 18a and 186b and the magnetic particles 10 can be coated with multiple different antibodies.

The functionalization of the sensor areas 18 can be performed by contact micro-arraying. The capture molecules can be passively adsorbed to the sensor areas, or bound using cross-linkers.

The functionalization of the magnetic particles can be performed through standard EDC, tosyl-activated or epoxy conjugation chemistries.

Magnetic particle sensors 60 can be embedded in the IC 16. The magnetic particle sensors 60 can be optical, magnetic, mechanical, acoustic, thermal, electromagnetic in nature, or combinations thereof. An array of magnetic particle sensors 60 can be embedded in the IC 16, where each magnetic particle sensor 16 can be individually addressable.

One or more magnetic concentration force generators can attract the magnetic particles 10 to the sensor areas 18. The magnetic concentration force generator(s) can be one or more electrical concentration conductors 62 embedded in the IC 16, directly above the magnetic particle sensors 60. Magnetic concentration forces also can be generated externally to the IC 16 using one or more permanent magnets or external electromagnets.

One or more magnetic separation force generators can be used to remove the non-specifically bound magnetic particles 68 from the sensor areas 18. The magnetic separation force generators can be one or more electrical separation conductors 64 embedded in the IC and located in proximity to the sensor areas. Magnetic separation forces also can be generated externally to the IC 16 using one or more permanent magnets or external electromagnets.

One method of fabricating and integrating the magnetic particle sensors 60, the magnetic concentration force generators and the magnetic separation force generators is described in PCT International patent application serial no. PCT/US09/031155, filed on Jan. 15, 2009, and provisional application 61/021,861, filed on Jan. 17, 2008, both of which are incorporated herein by reference in their entirety.

The device can perform immuno-assays in a sandwich capture format.

To perform the assay, about 15 µl of a sample, such as but not limited to a 15 µl whole blood sample 32 can be delivered onto the top of the membrane filter 2. The membrane filter 2 can trap the whole blood cells 34 without lysing them, while allowing the filtrate 38 containing the soluble molecules including the target analyte 36 to pass. After traversing the membrane filter 2, the filtrate 38 can flow into the inlet of the capillary channel 6, where the dried magnetic particles 10 can be re-suspended and can flow along with the filtrate 38 through the length of the capillary channel 12 via capillary action.

Without assistance, the viscous plasma filtrate does not readily flow from the bottom of the filter 2, which has small pore size, into the capillary 12, which has a larger inner-diameter. In order to avoid having to apply pressure or use a large sample volume, dried reagents can be placed at the inlet 6 to the capillary 12, in proximity to the filter 2. The filtrate 38 presented at the bottom of the filter 2 can be attracted by the strongly hydrophilic dried reagents. Once in the inlet 6 of the capillary 12, the dried reagents can dissolve and capillary force can be sufficient to pull the filtrate the rest of the distance through the capillary 12 to the sensor areas 18.

Without the dried reagents at the inlet of the capillary 6, manufacturing variations can result in larger than expected separation between the bottom surface of the filter 2 and the inlet 6 of the capillary 12, or in misalignments where the inlet 6 of the capillary 12 is not flush with the bottom surface of the filter 2, which would prevent the flow of the filtrate 38 into the capillary 12.

The dried magnetic particles 10 in the bulking agent 8 can be placed at the inlet 6 of the capillary 12 to pull the filtrate 38 from the bottom of the filter 2 into the capillary 12.

Once in the capillary 12, the magnetic particles 10 can re-suspend and flow with the filtrate 38 along the length of the capillary 12. While flowing through the capillary 12, the magnetic particles 10 can bind to the target analyte 36 in the filtrate 38.

The length, diameter and hydrophobicity of the capillary 12 can be varied to control the flow rate and the magnetic particle incubation times. For faster flow through the capillary 12 the length and width can be reduced to about 0.5 mm and about 0.25 mm, respectively. For slower flow, the length and width of the capillary 12 can be increased to over about 10 cm and about 5 mm, respectively.

The capillary outlet 14 can be hydrophilic. The filtrate 38 can create a hanging drop 42 from a hydrophilic capillary outlet 14. The integrated circuit 16 can be oriented horizontally, for example, close enough to the capillary outlet 14 to allow the hanging drop 42 to flow onto the sensor areas 18. The size of the gap can range from under 0.1 mm to 2 mm, above which point the size of the drop 42 no longer bridges the gap. After the hanging drop 42 flows onto the surface 20 of the integrated circuit 16, the magnetic particles 10 in the filtrate 38 can sediment on the sensor areas 18.

The magnetic particles 10 sediment via gravity and magnetic forces to the surface 20 of the IC 16. 2 mA of current through the 2 μm wide concentration conductors 62 pulls the 4.5 μm magnetic particles 10 toward the sensor areas 18 with 1.1 pN of force.

In the presence of the target analyte 36, the magnetic particles 10 bind sediment to the sensor area 18 on the surface 20 of the IC 16 and bind strongly through specific bio-chemical or inorganic interactions. In the absence of the target analyte, the magnetic sediment to the sensor area 18 on the surface 20 of the IC 16 and bind weakly through non-specific interactions.

In an immuno-assay capture format, the magnetic particles 10 capture the target analyte 36 during sedimentation and bind to the sensor areas 18 on the surface 20 of the integrated circuit 16.

In order to count the number of specifically bound magnetic particles 10a in the sensor areas, the non-specifically bound magnetic particles 10b can be removed. The non-specifically bound magnetic particles 10b can be removed by magnetic forces, fluidic forces, electrostatic forces, or a combination thereof.

To perform an immuno-assay, the magnetic separation forces can be sufficiently strong to pull the non-specifically bound particles about 10b (>0.1-10 pN), away from the sensor areas 18, but not overly strong so as to remove the specifically bound magnetic particles about 10a (<60 pN). About 50 mA of current flowing through the about 5 um wide separation conductors 64 placed about 18 um from the about 4.5 um magnetic particles 10 pulls them about 1.1 pN of force. However, since the magnetic particles 10 can be pivoting on the surface 20 of the IC 161, the magnetic separation force on the last molecular tether can be amplified by the mechanical leverage effect resulting from the difference in lengths of the moment arms of the molecular tether and the separation force. The about 1.1 pN lateral magnetic force translates into a tensile about 7.5 pN force on the non-specific bond, sufficient to remove non-specifically bound particles 10b.

After application of the magnetic separation forces, and after removal of the non-specifically bound magnetic particles 10b from the sensor areas 18, the specifically bound magnetic particles 10a remaining in the sensor areas can be detected by the sensors 60b embedded in the IC. The number of specifically bound magnetic particles 10a in the sensor areas corresponds to the concentration of one or more target analytes 36 in the sample 32.

Magnetic particle sensors 60e can be placed outside the sensor areas in order to count the number of non-specifically bound magnetic particles 10b that have been removed from the sensor areas 18. The magnetic particle sensors 60e can count the total number of magnetic particles 10 that have settled onto the surface 20 of the IC 16, to compensate for any variation.

One method of performing the magnetic particle assay on the surface 20 of the chip 16 is described in PCT International patent application serial no. PCT/US09/031155, filed on Jan. 15, 2009, and U.S. Provisional Application No. 61/021,861, filed on Jan. 17, 2008, both of which are incorporated herein by reference in their entirety.

The IC 16 can contain digital electronics for identifying the quantity of target analytes 36, processing and displaying the assay results. The assay results can be numerically combined with on-chip calibration curves and the product can be encrypted and transmitted. In addition or separately, electronic sensors can be on the IC 16 or alongside the IC 16. The electronic sensors can be temperature, inertial, moisture sensors, and combinations thereof. The electronic sensors can be integrated on the IC 16. Timers to control the assay protocol can be integrated on the IC. Capacitive or resistive integrated circuit sensors can be used to detect moisture along the edges of the sensor areas 18. The moisture sensors can ensure that the filtrate 38 has flowed over the entire sensor area 18 on the surface 20 of the IC 16. These moisture sensors can also be used to start and control the on-chip protocol. A vibrating device can be combined with the device of the present invention. This device can vibrate while the magnetic particles 10 flow through the capillary 12 and settle to the surface 20 of the IC 16 to accelerate incubation times.

Various degrees of multiplexing can be employed. The magnetic particles 10 and the sensor areas 18a and 18b on the surface 20 of the IC 16 can be coated with one or more chemicals for the detection of multiple target analytes 38 at one time (i.e., concurrently). The one or more detection chemicals can be spatially segregated on the surface 20 of the IC 16 through micro-arraying such that different sensor areas 18a and 18b on the same IC 16, or different magnetic particle sensors 60 within one sensor area 18 can be coated with different detection chemicals.

Two or more capillaries 12a and 12b can hold magnetic particles functionalized with different detection chemicals, 10c and 10d. The capillaries 12c and 12d can lead to the same sensor area 18 or the capillaries 12a and 12b can lead to different sensor areas 18a and 18b on the same IC 16. Two or more filters 2a and 2b can be fitted to multiple capillaries 12a and 12b that lead into the same sensor area 18 or different sensor areas 18a and 18b on the same IC 16. The different filters 2a and 2b and different capillaries 12a and 12b can hold different magnetic particles coated with different chemicals. One filter 2 can be spatially segregated into unconnected sub-filters by patterned hydrophobic barriers or by fabricated and assembled bulk structures.

The above described degrees of multiplexing can be used to perform assay calibration curves concurrently with the detection and quantitation of the target analyte 38. A negative control can be performed, for example, where a portion of the sensor area 18 can be coated with a prevention chemical that can prevent a binding with the surface of the magnetic particles 10, such as casein or albumin. The negative control can indicate the amount of non-specific interaction occurring in the sample under test. In addition or separately, a positive control can be performed where a portion of the sensor areas 18 can be coated with an activation chemical to ensure binding with the surface of at least a portion the magnetic particles 10, such as one or more of the target analytes 38. An entire calibration curve can be performed alongside the measurement of the target analyte 38 for accurate quantitation.

A plurality of capillaries 12c and 12d can be used for faster transfer of the filtrate 38 to the IC 16. In addition, the capillary channels 12 can be filled with a wicking material like glass fiber or nitro-cellulose for faster transfer of filtrate 38 to the IC 16.

For improved filtration characteristics, a membrane filter assembly containing multiple membrane filters 2c and 2d of varying characteristics can be stacked above the inlet of the capillary 6. Each filter can be loaded with different dried proteins, reagents, chemicals and magnetic particles.

The device can be configured without capillaries. The magnetic particles 10 can be dried in or to the bottom of a porous material like a membrane filter 2 or a nitro-cellulose strip. The membrane filter 2 can be placed at a small distance above the top of the chip.

The system can have a sedimentation capillary 84 and a delivery capillary 92. The inlet 94 of the delivery capillary 92 can be placed directly below the filter 2 and delivers the filtrate 38 into the sedimentation capillary 84. This delivery capillary 92 can have dried reagents 82 at the inlet 94 to facilitate the flow of the filtrate 38 from the bottom of the filter 2 into the capillary 92. The delivery capillary 92 can be position such that the filtrate 38 flows laterally from the bottom of the filter 2 to the sedimentation capillary 84. The sedimentation capillary 84 can be placed vertically directly above the sensor area 18 and the delivery capillary 92 can join to the sedimentation capillary 84 at any point along the height of the sedimentation capillary 84, for example in the middle. The delivery and the sedimentation capillaries 92 and 84 can be manufactured in a single plastic capillary cartridge 80. The capillaries in the cartridge 80 can be manufactured using plastic embossing, injection molding or photolithography. A lyophilized microsphere 90 can be placed in the inlet 86 at the top of the sedimentation capillary 84.

A drop of whole blood 32 can be placed on the membrane filter 2. The whole blood cells 34 can be trapped in the membrane 2, and the filtrate 38 containing the target analytes 36 flow through into the inlet 94 of the delivery capillary 92. The filtrate 38 can flow through the delivery capillary 92 and into the sedimentation capillary 84. The filtrate 38 can then flow downward to the sensor area 18 on the surface 20 of the IC 16, and upward to the microsphere 90. The filtrate 38 can flow onto the sensor area 18 and across the surface 20 of the integrated circuit 16 before the filtrate 38 reaches the microsphere 90 such that the filtrate 38 can be no longer flowing through the sedimentation capillary 84 by the time the filtrate reaches the microsphere 90.

Upon contact with the microsphere 90, the bulking agent 8 can become solubilized. For example, when there is no flow, the soluble bulking agent 98 can be stationary, i.e., not flowing in any direction. The diffusion of the solubilized bulking agent 98 can be slow, and can be exceeded by the sedimentation rate of the magnetic particles 10 via gravity or a magnetic concentration force. The magnetic particles 10 sediment out of the solubilized bulking agent 98, through the sedimentation capillary 84 onto the sensor area 18 at the surface 20 of the integrated circuit 16. The magnetic particles 10 bind to the surface 20 of the IC 16 in the sensor area 18 in the presence of one or more target analytes 36, and the assay protocol can proceed as described previously.

Packing or inserting of the microspheres 90 can be replaced by simply placing the microspheres at the top inlet 86 of the sedimentation capillary 84, facilitating manufacturing.

The incubation time of the magnetic particles 10 with the filtrate 38 can be precisely controlled by the length of the sedimentation capillary 84, for high accuracy applications. About 4.5 um magnetic particles 10 can settle gravitationally at about 0.4 mm/min in plasma, so about a 4 mm sedimentation capillary height 154 could result in about a 10 minute incubation time.

Mixing can be reduced or eliminated since as the magnetic particles 10 sediment through the sedimentation capillary 84, the magnetic particles 10 can bind with all the analyte 36 in the path of the magnetic particles 10.

The solubilized bulking agent 98 can interfere with the performance of the assay. To mitigate this effect, less than about 0.1 µL of bulking agent can be placed at the inlet of the delivery capillary 94. The less than about 0.1 µl of bulking agent can be diluted approximately times by about 15 µl of plasma. The solubilized bulking agent 98 from the larger 7.5 µl microsphere cannot interfere with the assay since the microsphere does not have enough time to diffuse to the sensor area 18 from a distance of about 4 mm.

The sedimentation capillary 84 can be filled with more than one adjacent regions of fluid, i.e. different buffers loaded in series in the capillary channel 84. In the absence of turbulent flow, these regions of fluid only mix at the interface due to diffusion processes. The magnetic particles 10 sediment much quicker than the diffusion of the fluids so the magnetic particles 10 can sediment through all the different regions of fluid faster than they can mix. This functionality can be useful for exchanging buffers for nucleic acid amplification reactions. The sedimentation capillary 84 can be filled with a lysis buffer 110, an isothermal amplification buffer 112 and a detection buffer 114. Laminar flow from for example the delivery capillary 92 can cause the lysis buffer to contact the microsphere 90 at the top of the sedimentation capillary 84 and re-solubilize it, re-suspending the magnetic particles 10. The magnetic particles 10 can capture the target oligonucleotides as the magnetic particles 10 traverse the lysed organic matter in the lysis buffer 110, the target oligonucleotides can be amplified as the magnetic particles 10 traverse through the amplification buffer 112 and finally the magnetic particles 10 enter the detection buffer 114 which allows them to bind to the surface 20 of the IC 16. The sedimentation capillary 84 can be pre-loaded with the different regions of fluid or the delivery capillary can fill the sedimentation buffer with the desirable regions of fluid. The reagents needed to generate the regions of fluid can be dried in a capillary and re-solubilized by the sample.

A second, wider capillary 70 can be placed above the membrane filter 2 for easy collection of the sample, such as whole blood from a finger stick. This capillary can range from 0.25 mm to 1 cm in diameter and 1 mm to 5 cm in length. As a general rule, the diameter of capillary 70 should be bigger than the diameter of the capillary 12 in order to permit the flow of the filtrate.

Anticoagulants such as heparin, sodium citrate and ethylenediaminetetraacetic acid can be dried and placed on the top of the membrane, at the bottom of the membrane, in the inlet of the capillary, along the inner sides of the capillary or on the surface of the IC.

The capillary channel can be functionally replaced with or used in additional with a microfluidic system that can further process the analyte in a microfluidic system before delivering the analyte to the IC.

Functionalities can be added to the microfluidic chamber (valving, pumping, thermal heating) to mix or separate fluids or fluidic contents and/or lyse whole blood cells and nucleus to conduct DNA amplification.

The magnetic particle sensors 60 can be optical sensors 104a and b embedded in the IC, with an external source for illumination 100. Magnetic particles 10c and d on the surface 20 of the integrated circuit 16 cast a shadow 102 that can reduce the amount of light transmitted from the light source 100 to the optical sensor 104b. The optical sensor 104b detects the magnetic particle 10c by measuring the reduction of incident light. The integrated circuit 16 can have a surface that transmits light, such as although not limited to silicon dioxide.

The optical sensors 104a and b can be implemented as but not limited to active pixel sensors, charge-coupled devices, avalanche photodiodes, PIN photodiodes, or other solid state optical detectors.

One or more source of illumination 100 can be situated directly above the integrated circuit 16 such that the shadows from the magnetic particles project downward. One or more sources of illumination 100 can illuminate the surface 20 of the integrated circuit 16 indirectly and/or at oblique angles. The source of illumination 100 can be placed above the capillary that flows the filtrate 38 onto the surface 20 of the IC 16.

Alternatively, the magnetic particles 10 can be detected optically externally to the IC, with a CCD camera from above or below the IC, for example.

From the foregoing, it will be appreciated that the platform described can be used for many applications, including, but not limited to, the following.

1. Diagnostics:
   (a) Simplex assays;
   (b) Parallel or multiplexed assays;
   (c) DNA micro-array assays;
   (e) Glucose, cholesterol, metabolites, small molecules detection.
2. Environmental assays:
   (a) Food contamination;
   (b) Water/soil contamination.
3. Proteomics:
   (a) Protein-protein binding force measurements;
   (b) Protein-protein binding resonant frequencies;
   (c) Protein kinetics research.
4. Genomics:
   (c) DNA methylation profile;
   (d) DNA force measurements.
5. Magnetic Particle AFM:
   (a) Low 1/f noise AFM;
   (b) AFM with digitally controlled force and frequency;
   (c) Multiplexed AFM
6. Magnetic Particle Characterization:
   (a) Exploration of magnetic properties of particles of different sizes and characteristics.
7. Low Cost Bio-sensor Networks:
   (a) Integrated and direct wireless transmission of assay results;
   (b) Real-time outbreak/contamination monitoring.

FIG. 1 is a three dimensional view of the sample preparation and detection system 1. The system 1 may be positioned adjacent an IC, or may be a completely integrated preparation and detection system that can include one or more IC detectors/sensors. The system 1 can be configured to be positioned adjacent, or integrated with an IC such as that disclosed in PCT International patent application serial no. PCT/US09/031155, filed on Jan. 15, 2009, and U.S. Provisional Application No. 61/021,861, filed on Jan. 17, 2008, both of which are incorporated herein by reference in their entireties. The sample preparation system 1 may be configured to operate in cooperation with, or be integrated with, other types of sensor devices such as temperature, inertial, and moisture sensors.

Figure 2:
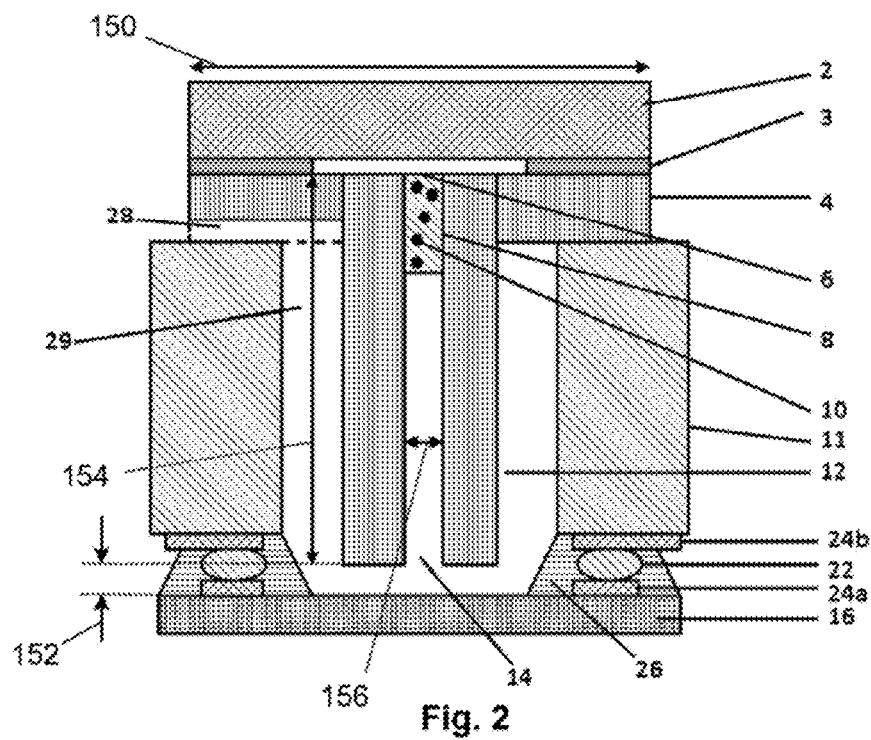

As shown in FIGS. 1 and 2, the system 1 can have a filter support structure 4 that can be mounted on the top surface of a printed circuit board 11 directly above an opening 29 formed in the printed circuit board 11. An adhesive ring 3 can attach the filter support structure 4 to a membrane filter 2. The membrane filter 2 can be cylindrical, or have a generally oval, square, triangular, or rectangular cross-section. The membrane filter 2 can have a membrane filter width or diameter 150 that can be from about 0.5 mm to about 20 mm, more narrowly from about 1 mm to about 8 mm, for example about 4 mm. The peripheral shape and size of the membrane filter 2 and the filter support structure 4 can be the same or different.

A ventilation channel 28 can be formed by a radial groove in the bottom surface of the filter support structure 4 and/or the top surface of printed circuit board 11. An integrated circuit 16 can be attached to the bottom side of printed circuit board 11 for example by a plurality of solder bumps 22. Solder bumps 22 can be attached to IC bond pads 24a and printed circuit board metallization 24b, thus providing mechanical attachment and electrical interconnection between the integrated circuit 16 and the printed circuit board 11. A polymer seal 26 can be placed between the integrated circuit 16 and the printed circuit board 11, forming a sealed cavity and protecting the electrical connections from contamination by fluids. A capillary channel 12 can be attached to the filter support structure 4, such that a capillary inlet 6 can be positioned directly below filter 2, and a capillary outlet 14 can be positioned directly above sensor areas 18 on the surface 20 of the integrated circuit 16.

The bottom of the capillary outlet 14 can be in contact with or separated from the surface 20 of the integrated circuit 16 by an IC gap 152. The IC gap 152 can be from about 0.05 mm to about 2 mm, more narrowly from about 0.1 mm to about 1 mm. The capillary channel 12 can have a capillary channel length 154 and a capillary channel diameter or width 156. The capillary channel length 154 can be from about 0.5 mm to about 20 mm, more narrowly from about 1 mm to about 8 mm, for example about 4 mm. The capillary channel width 156 can be from about 0.05 mm to about 2 mm, more narrowly from about 0.1 mm to about 1 mm, for example about 0.5 mm.

The magnetic particles 10 can be dried in a bulking agent 8 and placed in the capillary channel 12, for example near or at the inlet 6 and/or outlet 14 and/or along all or part of the length of the capillary channel 12.

Figure 3:
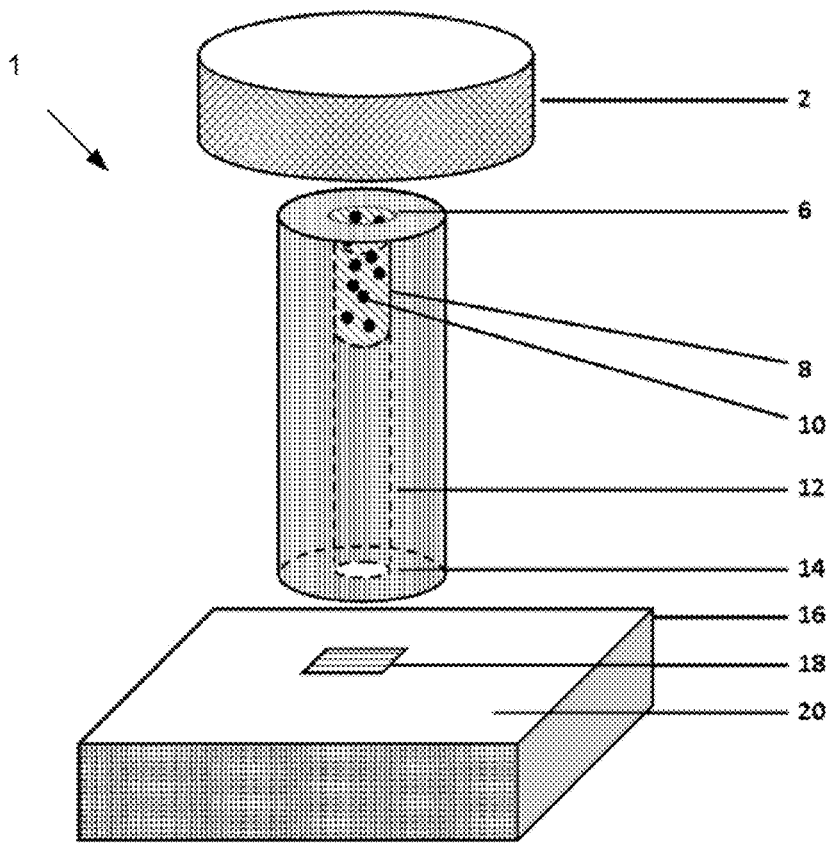
FIG. 3 is a perspective, exploded and partially see-through view of a variation of the system.

FIG. 3 illustrates that the filter 2 can be above the capillary channel 12. Dried magnetic particles 10 can be in a bulking agent 8 at the inlet 6 of the capillary channel 12. The outlet 14 of the capillary channel 12 can be placed directly over the sensor area 18 on the surface 20 of an integrated circuit 16.

FIGS. 4 through 8 are cross-sectional side views of the key components of the device and demonstrate the operation of the device for a sandwich capture immuno-assay format.

FIG. 4 shows the whole blood sample 32 containing whole blood cells 34 and one or more target analytes 36 placed on the top of the membrane filter 2.

FIG. 5 shows the filtrate 38 traversing to the bottom of filter 2. From the bottom of the filter 2, the filtrate 38 comes in contact with the highly hydrophilic bulking agent 8 at the inlet of the capillary channel 12. The hydrophilic bulking agent 8 pulls the filtrate into the capillary channel 12 and the magnetic particles 10 are re-suspended. The magnetic particles are coated with one or more capture antibodies 30 for binding to one or more target analyte 36.

Figure 6:
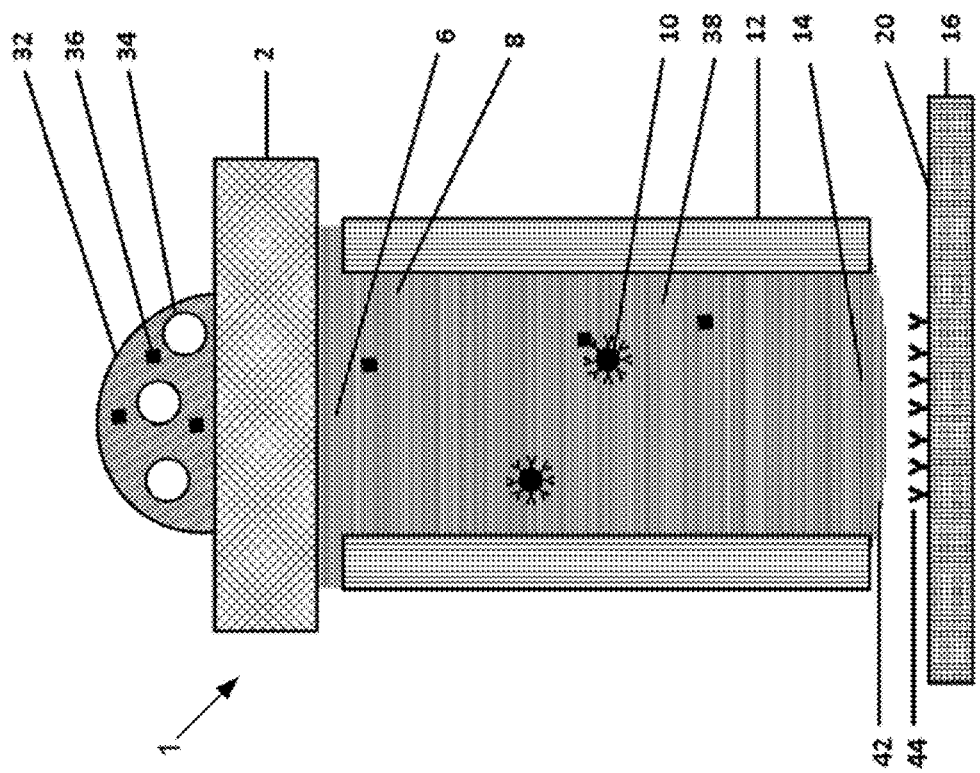

FIG. 6 shows the filtrate 38 flowing through the capillary channel 12. The filter 2 blocks the whole blood cells 34 from passing, but not the target analyte 36 which passes through into the capillary 12 where the re-suspended magnetic particles 10 bind to one or more target analytes 36. The flow due to capillary action pulls the filtrate to the surface 20 of an integrated circuit 16.

Figure 7:
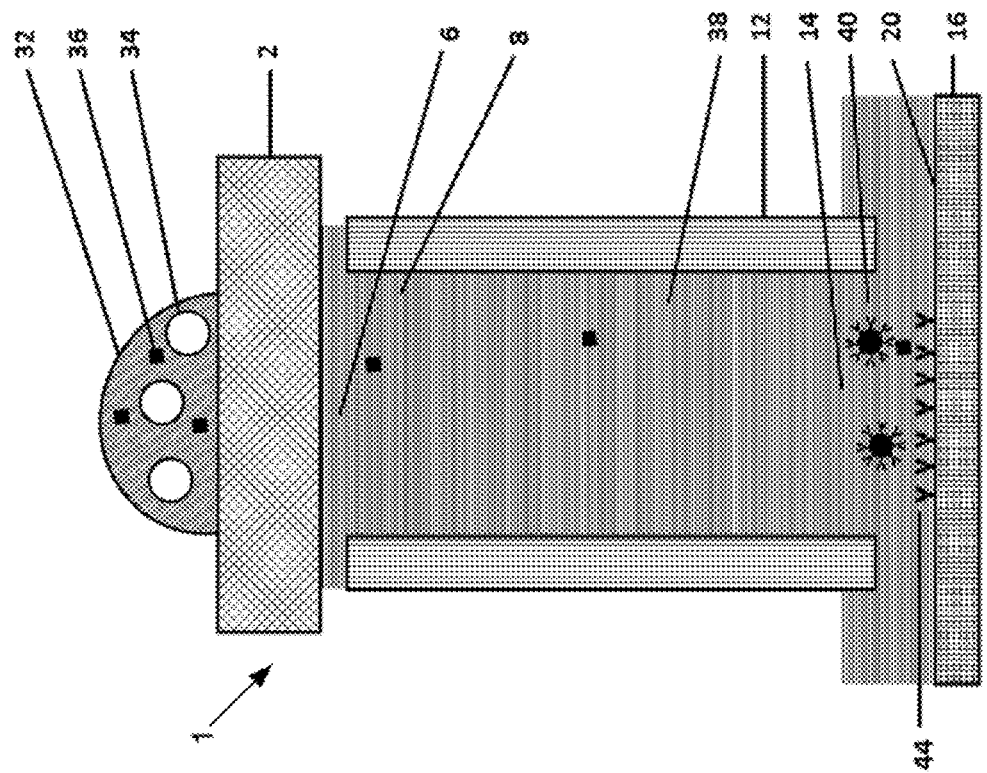

FIG. 7 illustrates the formation of a hanging drop 42 of filtrate 38 from the outlet 14 of the capillary channel 12. This drop will get larger until contacting the surface 20 of the integrated circuit 16, at which point the filtrate 38 will flow across the surface 20 of the integrated circuit 16.

Figure 8:
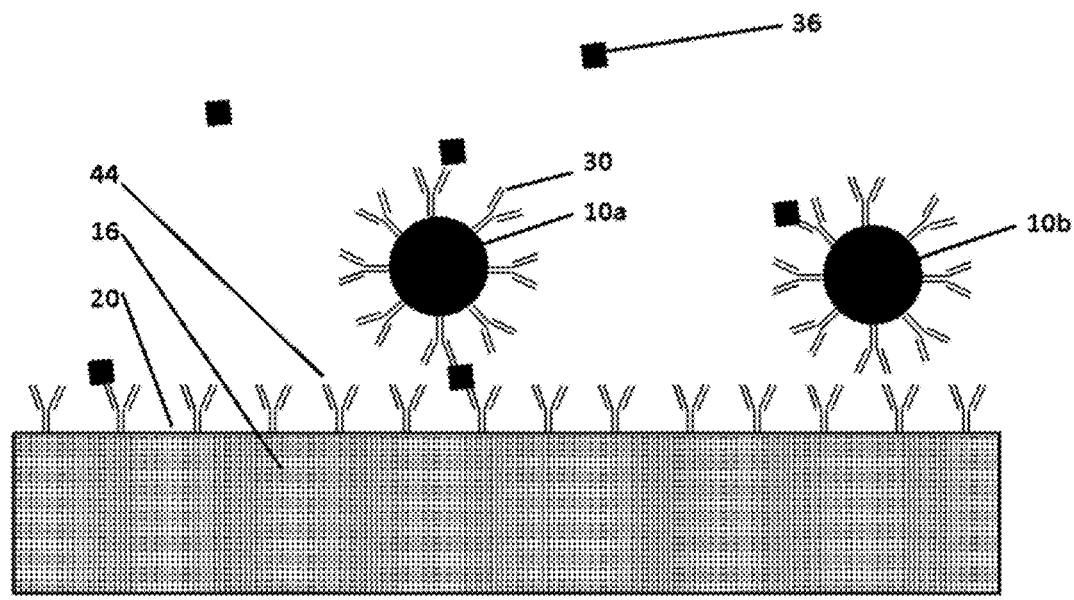
FIG. 8 is a side cross-sectional view of a variation of a method of performing the magnetic particle assay.

FIG. 8 shows how the filtrate 38 spread across the surface 20 of the integrated circuit 16. The magnetic particles 10 sediment to the surface 20 of the integrated circuit 16. The surface 20 can be coated with surface antibodies 44, and in the presence of one or more target analytes, the magnetic particles 10 can bind through strong specific interactions to the surface 20 of the integrated circuit 16.

Figure 9:
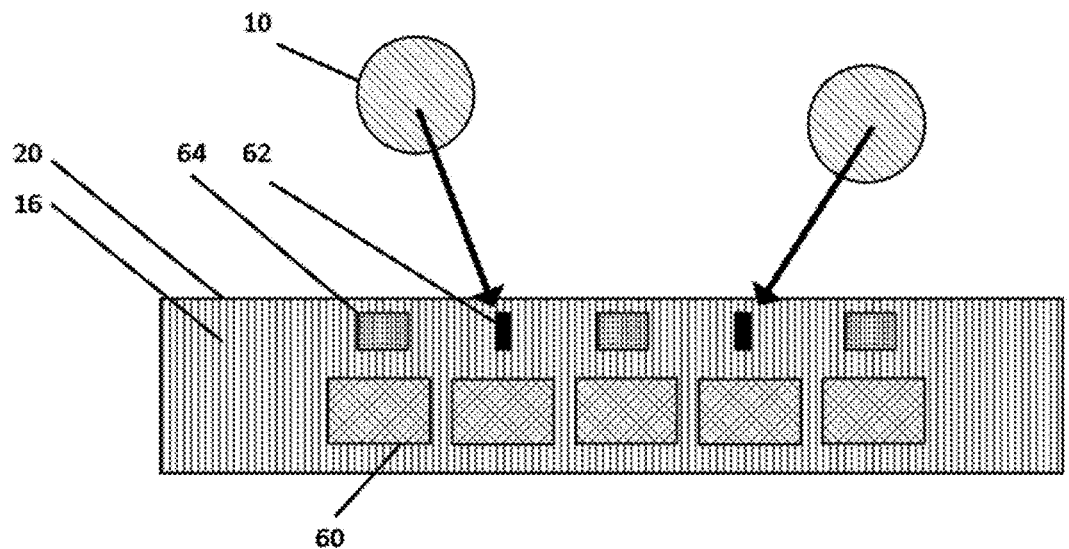
FIGS. 9 through 11 are side views of a variation of a method for using a variation of an integrated circuit.

FIG. 9 shows a close up view of two magnetic particles 10a and 10b at the surface 20 of the integrated circuit 16. Magnetic particle 10a can be specifically bound to the surface 20 through a specific immunological complex involving the surface antibody 44, the target analyte 36 and the capture antibody 30. Magnetic particles 10b has sedimented to the surface, but can be non-specifically bound, for example, since there is no immunological complex to strongly tether the magnetic particle 10b to the surface 20 of the integrated circuit 16.

Figure 10:
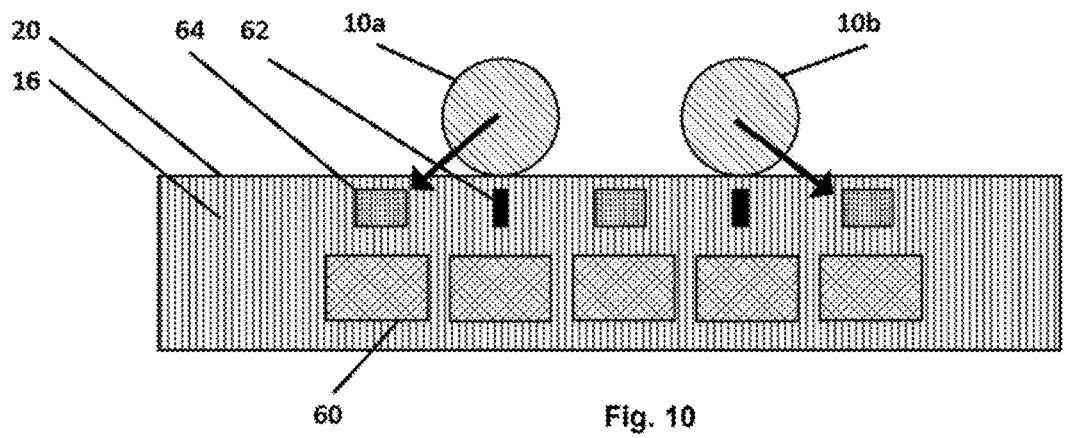
Figure 11:
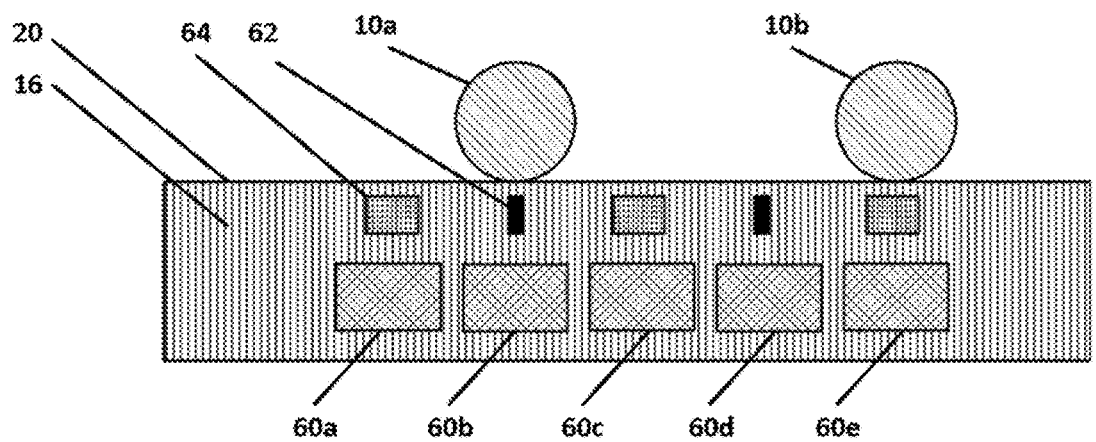

FIGS. 9-11 are cross-sectional views illustrating the operation of the integrated circuit 16.

FIG. 9 presents magnetic particles 10 as they sediment to the surface 20 of the integrated circuit 16. Current flowing out of the plane of view through the concentration conductors 62 pulls the magnetic particles to the surface 20 of the integrated circuit 16 directly above the concentration conductors 62.

FIG. 10 shows magnetic particles that can have settled onto the surface 20 of the integrated circuit 16. The current through the concentration conductors 62 can be turned off. As an illustrative example, magnetic particle 10a can be specifically bound to the surface 20, while magnetic particle 10b can be non-specifically bound to the surface 20. Current flowing out of the plane of view through the separation conductors 64 generated a magnetic force on the magnetic particles. The non-specifically bound magnetic particle 10b can be pulled toward the separation conductor, while the specifically bound magnetic particle 10a remains immobile.

FIG. 11 shows the magnetic particles after the non-specifically bound ones have been manipulated. The specifically bound magnetic particle 10a can remain immobilized to the surface 20, above the concentration conductor 62 and can be detected by sensor 60b. The non-specifically bound magnetic particle 10b can be pulled aside from the concentration conductor 62 and can remain immobilized on the surface 20 above the separation conductor 64 and can be detected by sensor 60e. In this case the integrated circuit 16 can detect one specifically bound magnetic particle (10a) indicating the presence of the target analyte. With a large number of magnetic and a large array of sensors 60, magnetic separation conductors 64 and concentration conductors 62, highly sensitive, multiplexed and quantitative assay can be performed.

FIG. 12 is a top view of the surface 20 of the integrated circuit 16. After the application of the magnetic separation forces, the specifically bound magnetic particle 10a remains in the sensor area 18. The non-specifically bound magnetic particle 10b can be pulled away from the sensor area. Note however, that both magnetic particles, 10a and 10b can be detected by sensors 60.

FIGS. 13 through 18 are three dimensional views of the various implementations of the sample preparation system. These various implementations can be used to perform various degrees of multiplexed assay.

Figure 13:
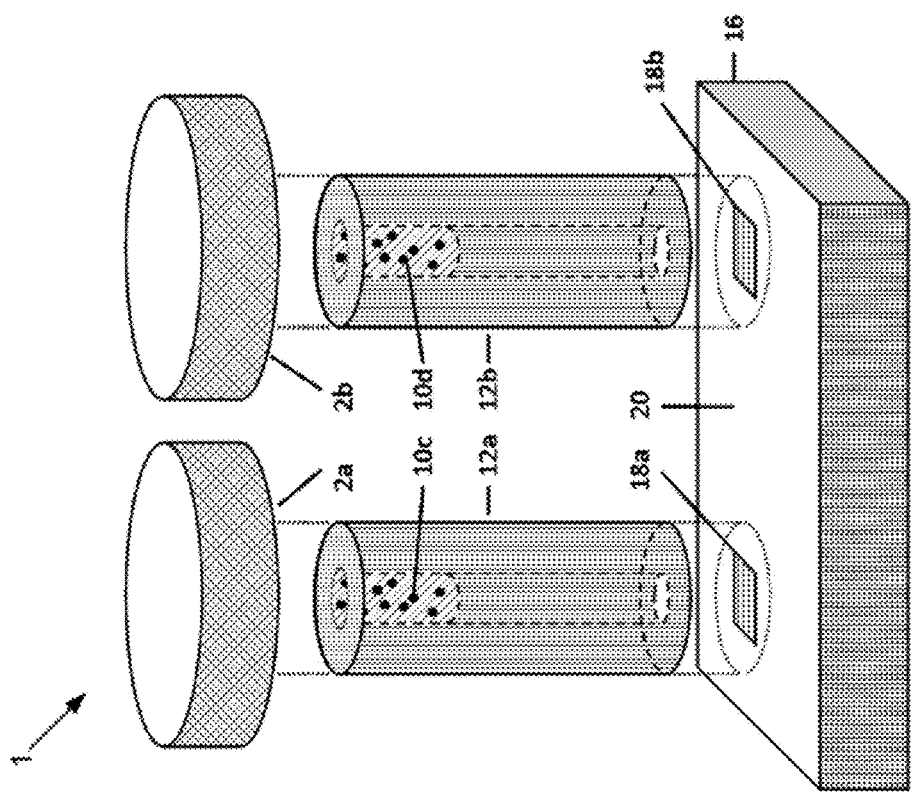

FIG. 13 shows two filters 2a and 2b in proximity to two capillaries 12a and 12b that can hold magnetic particles 10c and 10d functionalized with different detection chemicals. The capillaries 12a and 12b can deliver their respective filtrates to two different sensor areas 18a and 18b.

Figure 14:
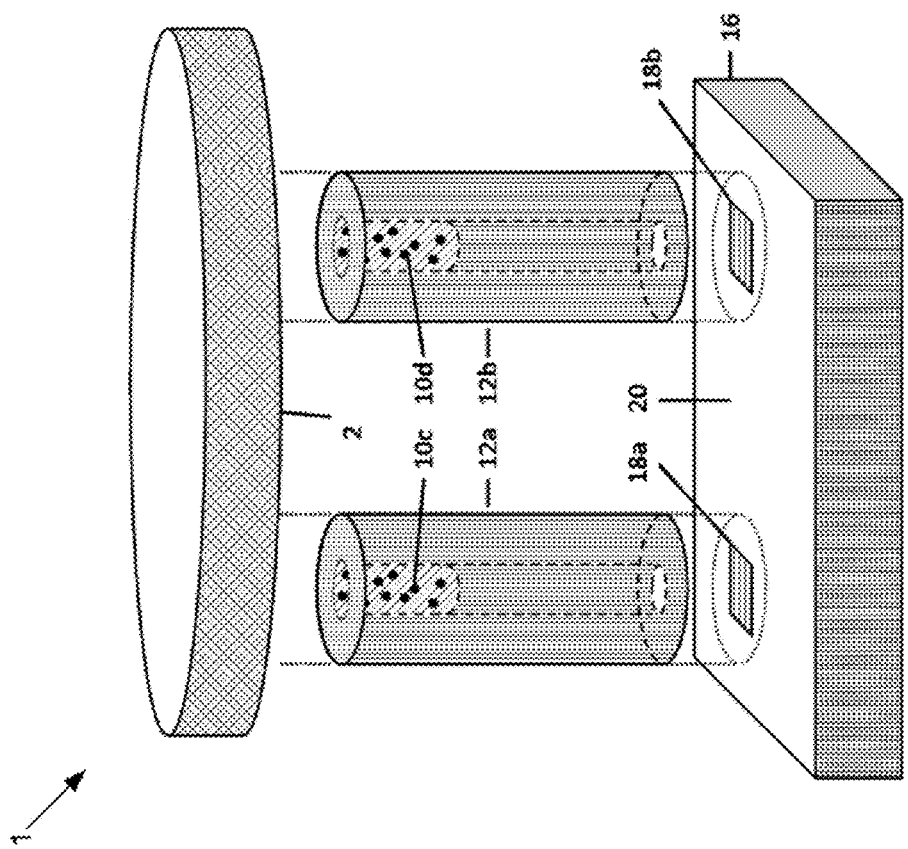

FIG. 14 shows one filter 2 in proximity to two capillaries 12a and 12b that can hold magnetic particles 10c and 10d functionalized with different detection chemicals. The capillaries 12a and 12b can deliver their respective filtrates to two different sensor areas 18a and 18b.

Figure 15:
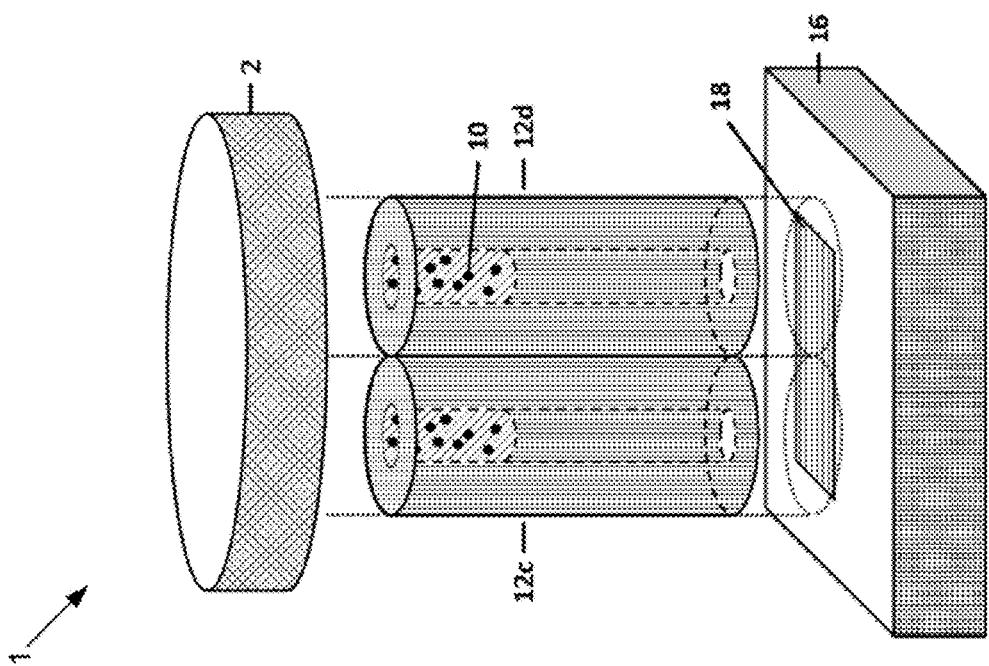

FIG. 15 shows one filter 2 in proximity to two capillaries 12a and 12b that can deliver their respective filtrates to the same sensor area 18.

Figure 16:
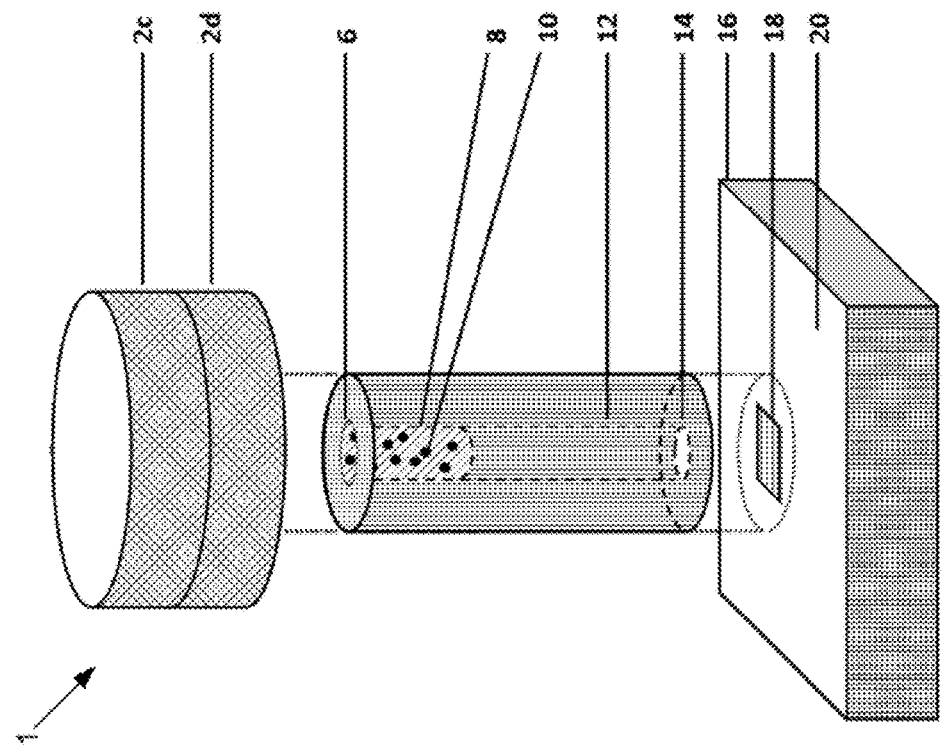

FIG. 16 shows two filters 2c and 2d stacked above one capillary channel 12.

FIG. 17 show a device configured without capillaries. The magnetic particles 10 can be dried in or to the bottom of a porous material like a membrane filter 2 or a nitro-cellulose strip. The membrane filter 2 can be placed at a small distance above the top of the chip.

Figure 18:
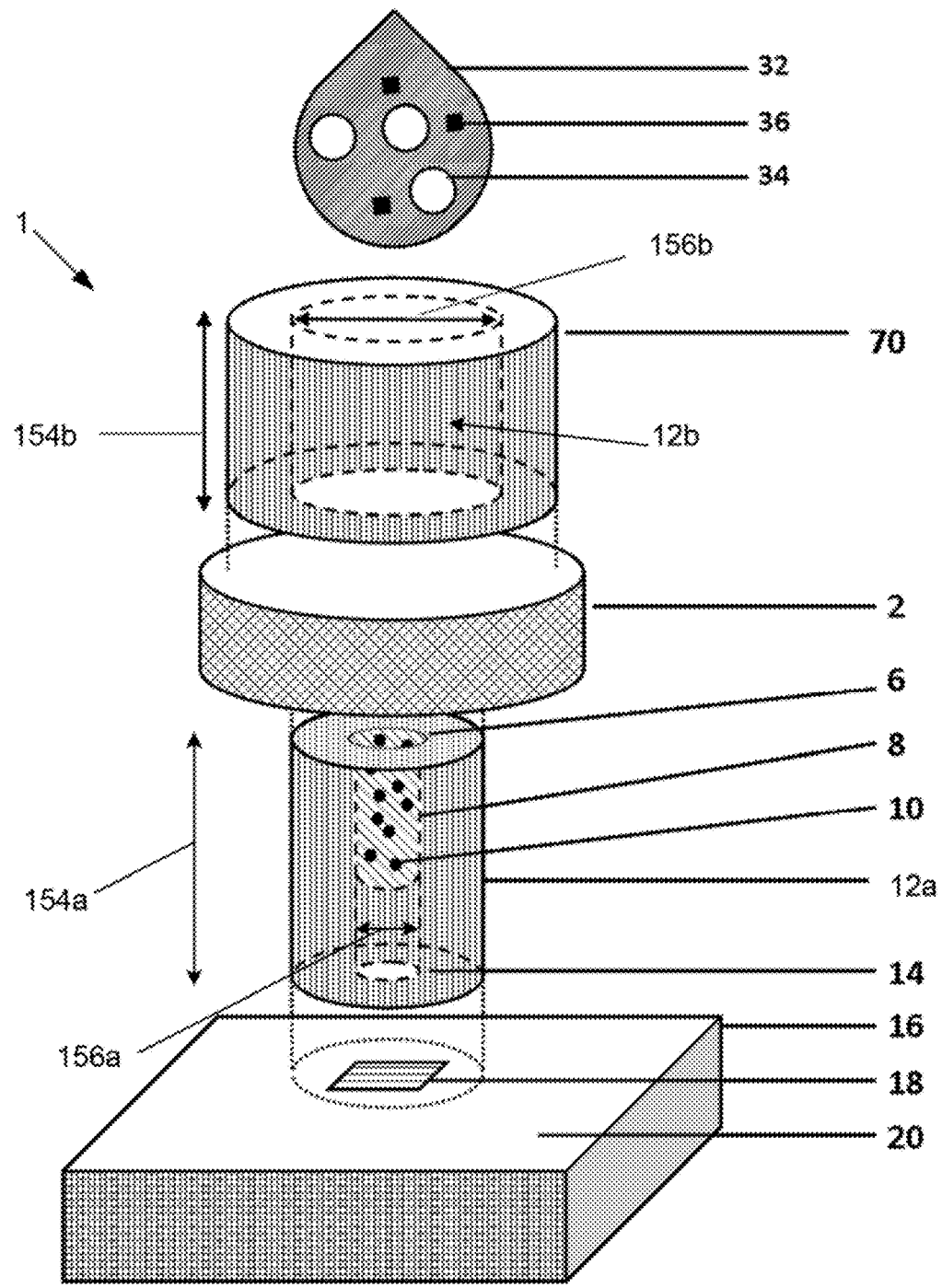

FIG. 18 shows that a second capillary 70 can be placed above the membrane filter 2, for example for collection of the sample, such as whole blood from a finger stick. The second capillary can have a second capillary channel 12b that can have a second capillary diameter 156b. The second capillary diameter 156b can be, larger, smaller or the same as the first capillary channel diameter 156a. The capillary channels 156a and 156b can be as listed elsewhere herein or from about 0.25 mm to about 1 cm, for example about 4 mm. The second capillary 70 can have a second capillary channel length 154b. The second capillary channel length 154b can be, larger, smaller or the same as the first capillary length 154a. The capillary channel lengths 154a and 154b can be as listed elsewhere herein or from about 1 mm to about 5 cm, for example about 5 mm. The diameter of second capillary 70 can be larger than the diameter of the first capillary 12, for example, to increase the flow of the filtrate.

Figure 19:
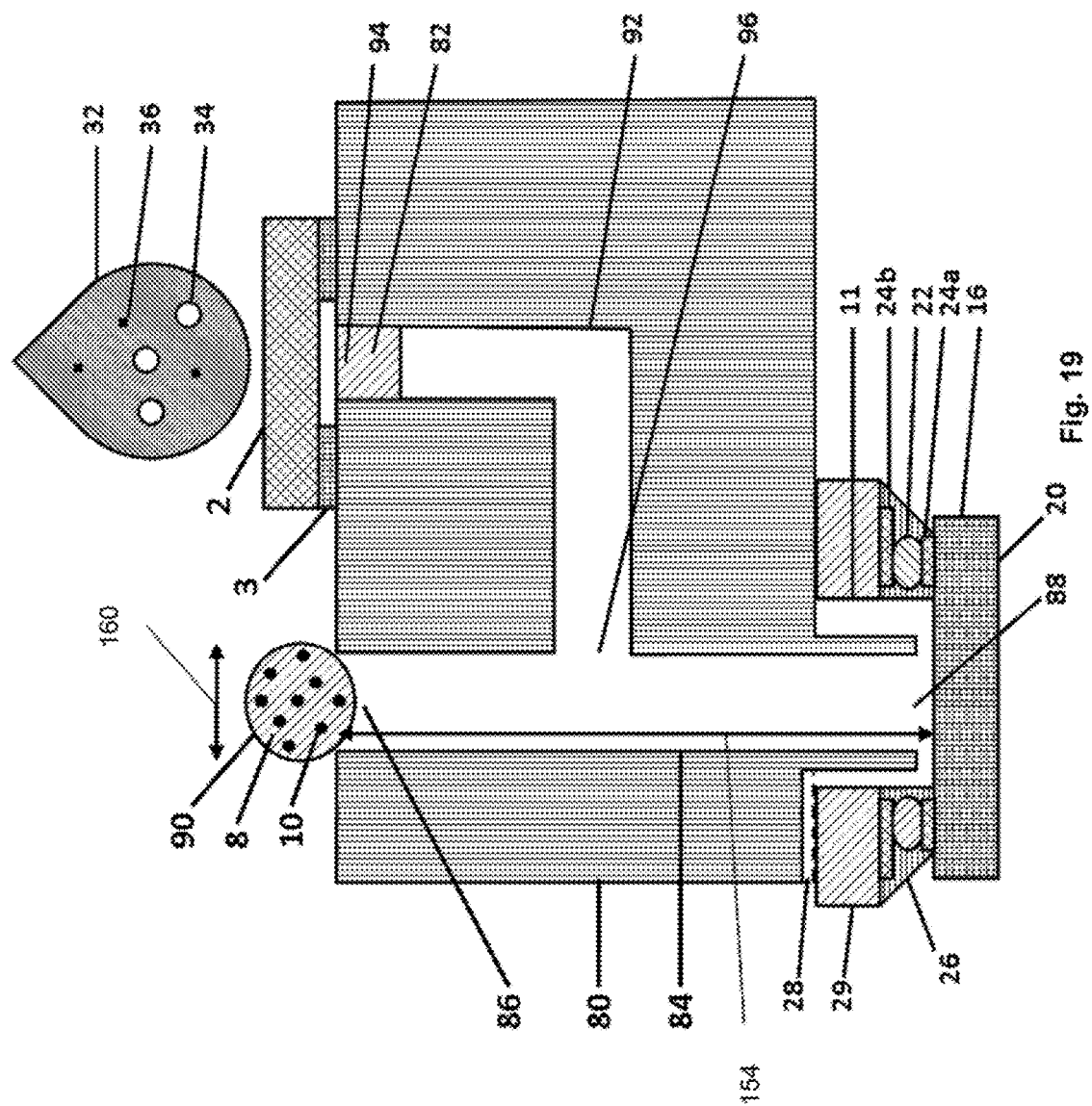
FIGS. 19 through 21 are cross-sectional views of a variation of a method for using a variation of the system.
Figure 20:
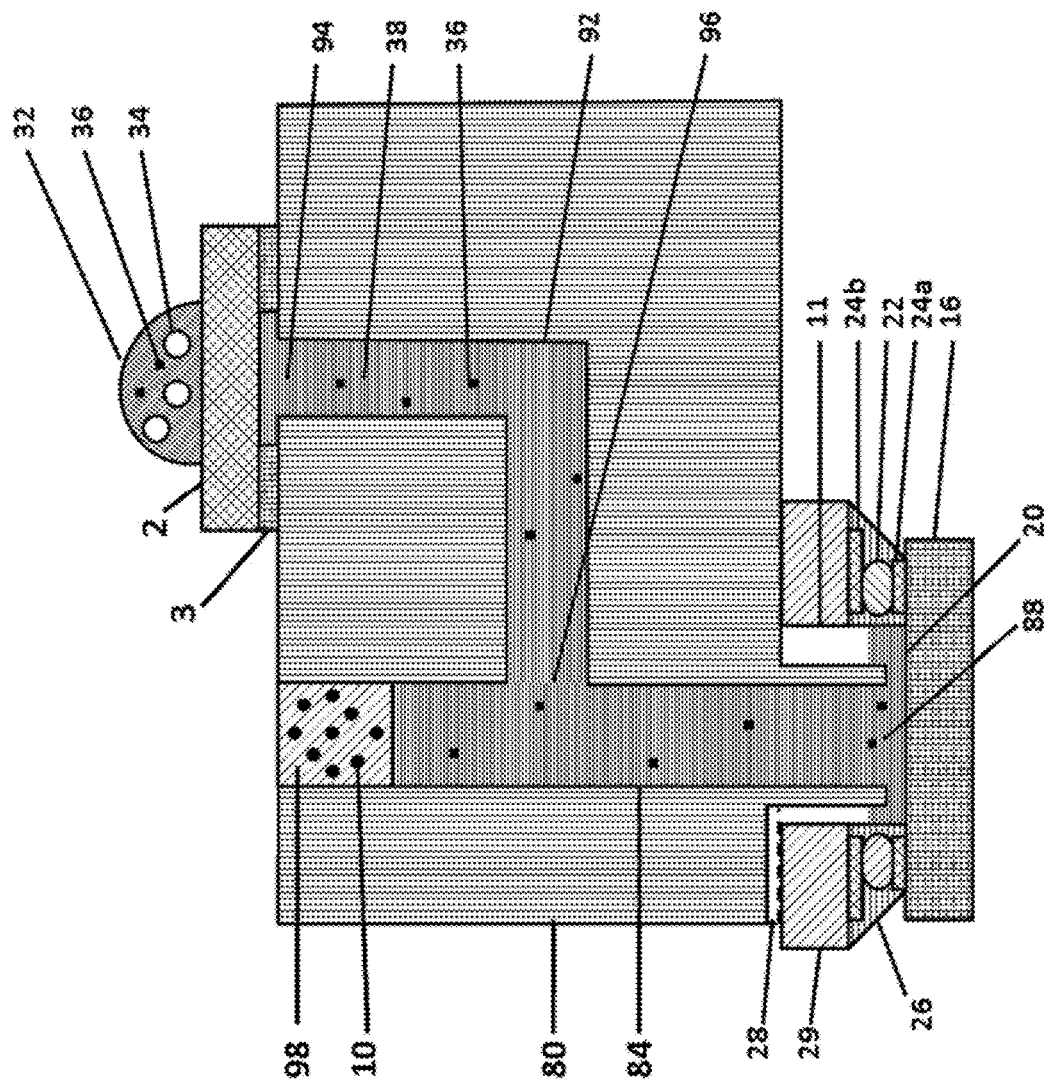
Figure 21:
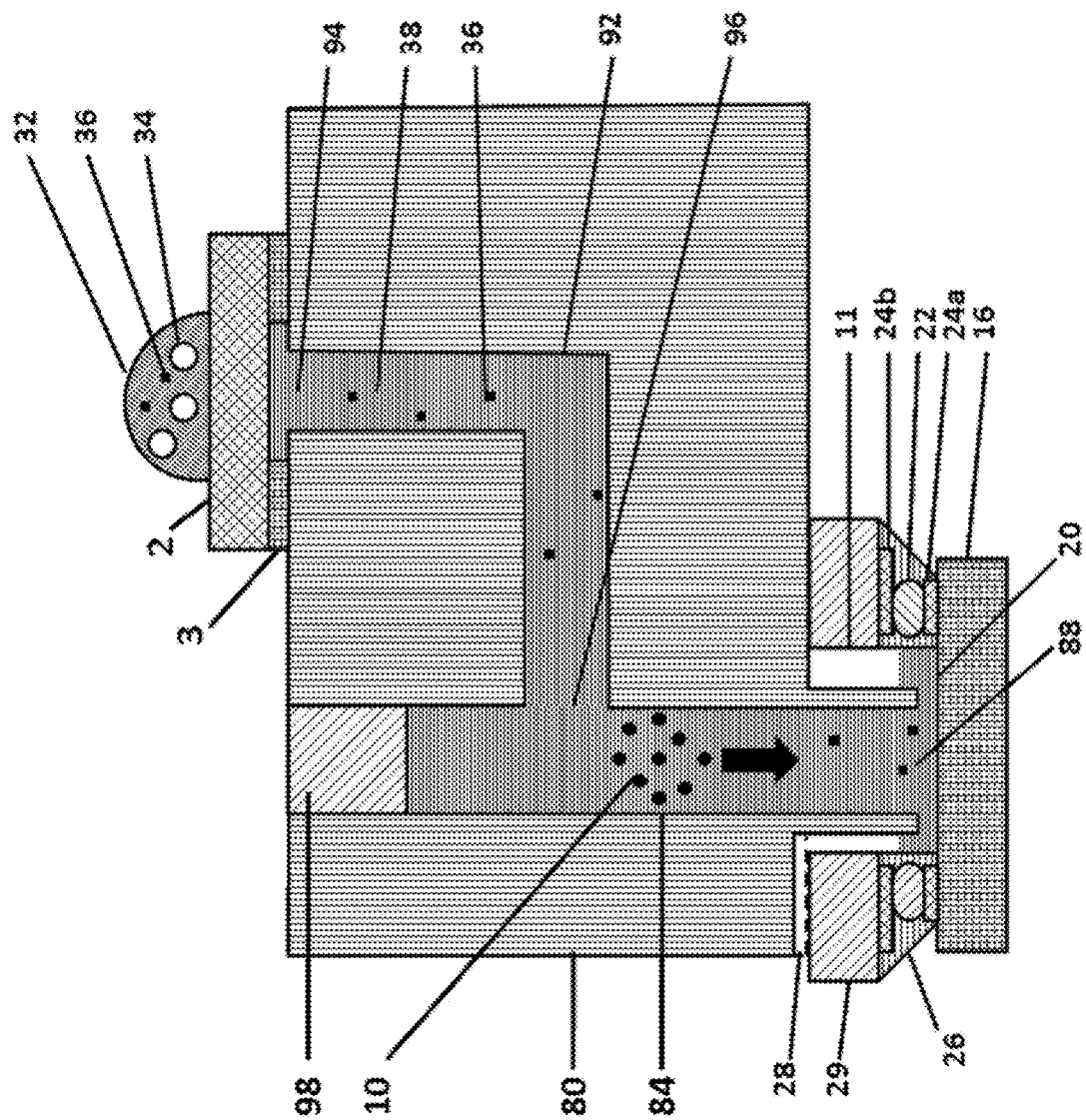

FIGS. 19 through 21 are cross-sectional views of an implementation with 2 capillary channels for better control of the assay protocol.

FIG. 19 shows the system with sedimentation capillary 84 and a delivery capillary 92. The inlet 94 of the delivery capillary 92 can be placed directly below the filter 2. The inlet 94 can be configured to deliver the filtrate 38 into the sedimentation capillary 84. The delivery capillary 92 can have dried reagents 82 at the inlet 94 to facilitate the flow of the filtrate 38 from the bottom of the filter 2 into the capillary 92. The delivery capillary 92 can be position such that the filtrate 38 flows laterally from the bottom of the filter 2 to the sedimentation capillary 84. The sedimentation capillary 84 can be placed vertically directly above the sensor area 18. The delivery capillary 92 can join to the sedimentation capillary 84 at any point along the height of the sedimentation capillary 84, for example in the middle. The delivery and the sedimentation capillaries 92 and 84 can be manufactured in a single plastic capillary cartridge 80. The capillaries in the cartridge 80 can be manufactured using plastic embossing, injection molding or photolithography. A lyophilized microsphere 90 can be placed in the inlet 86 at the top of the sedimentation capillary 84. The lyophilized microsphere 90 can have a microsphere diameter 160, for example, from about 0.1 mm to about 5 mm, more narrowly from about 0.5 mm to about 4 mm, for example about 2 mm.

FIG. 20 shows a drop of whole blood 32 placed on the membrane filter 2. The whole blood cells 34 can be trapped in the membrane 2. The filtrate 38 containing the target analytes 36 can flow through the inlet 94 of the delivery capillary 92. The filtrate 38 can flow through the delivery capillary 92 and into the sedimentation capillary 84. The filtrate 38 can then flow downward to the sensor area 18 on the surface 20 of the IC 16, and upward to the microsphere 90. The filtrate 38 can flow onto the sensor area 18 and across the surface 20 of the integrated circuit 16 before the filtrate 38 reaches the microsphere 90. The filtrate 38 can be no longer flowing through the sedimentation capillary 84 by the time the filtrate reaches the microsphere 90. Upon contact with the microsphere 90, the bulking agent 8 can solubilize.

FIG. 21 shows the magnetic particles 10 incubating with the target analyte 36. When there is no flow, the soluble bulking agent 98 can be stationary, i.e., not flow in any direction. The diffusion of the solubilized bulking agent 98 can be slow, and can be exceeded by the sedimentation rate of the magnetic particles 10 via gravity or a magnetic concentration force. The magnetic particles 10 can sediment out of the solubilized bulking agent 98, for example, through the sedimentation capillary 84 onto the sensor area 18 at the surface 20 of the integrated circuit 16. The magnetic particles 10 can bind to the surface 20 of the IC 16 in the sensor area 18 in the presence of one or more target analytes 36, and the assay protocol can proceed as described previously.

Figure 22:
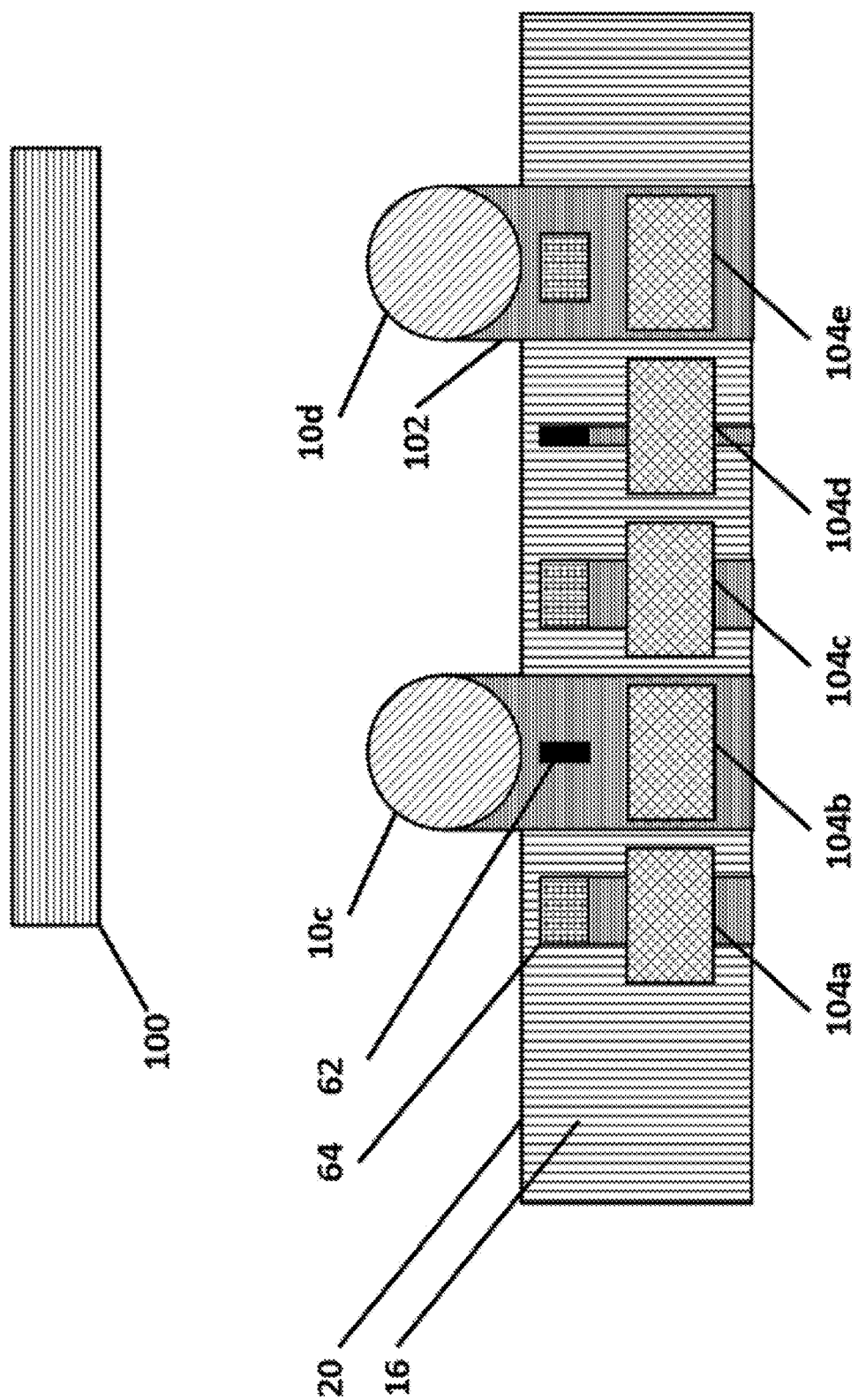
FIG. 22 is cross-sectional views of a variation of a method for using a variation of the integrated circuit.

FIG. 22 is a cross sectional view of the integrated circuit 16 with optical magnetic particle sensors 104*a* through 104*e*. The magnetic particle sensors 104*a* through 104*e* can be embedded in the IC. The system can have an external illumination source 100. The illumination source 100 can emit photons toward the IC. The illumination source 100 can emit visible light, invisible light (e.g., infrared, ultraviolet), or combinations thereof. Magnetic particles 10*c* and 10*d* on the surface 20 of the integrated circuit 16 can cast a shadow 102 that can reduce the amount of light transmitted from the light source 100 to the optical sensor 104*b*. The optical sensor 104*b* can detect the quantity of magnetic particle 10*c* by measuring the reduction of incident light. The integrated circuit 16 can have a surface that can transmit light, such as although not limited to silicon dioxide. Also, the concentration conductors 62 and the separation conductors 64 can be thinner than the diameter of the magnetic particles 10, for example to detect most or every magnetic particle.

The optical sensors 104*a* and 104*b* can be active pixel sensors, charge-coupled devices, avalanche photodiodes, PIN photodiodes, other solid state optical detectors, LEDs, or combinations thereof.

FIGS. 23 through 25 are partial cross sections of an implementation in which the magnetic particles are incubated with different fluids sequentially.

FIG. 23 shows the sedimentation capillary 84 filled with more than one regions of fluid, i.e. different buffers loaded in series in the capillary channel 84. In the absence of turbulent flow, these regions of fluid only mix at the interface due to diffusion processes. Capillary action can pull these regions of fluid to the top of the sedimentation capillary 84 where lies a microsphere 90. The sedimentation capillary 84 can be filled with a lysis buffer 110, an isothermal amplification buffer 112 and a detection buffer 114.

FIG. 24 shows that once the uppermost region of fluid reach the microsphere, the bulking agent 8 solubilized into a solubilized bulking agent 98.

FIG. 25 shows the magnetic particles 10 sedimenting much quicker than the diffusion of the fluids so the magnetic particles 10 can sediment through all the different regions sequentially. The magnetic particles 10 can capture the target oligonucleotides as the magnetic particles 10 traverse the lysed organic matter in the lysis buffer 110, the target oligonucleotides can be amplified as the magnetic particles 10 traverse through the amplification buffer 112 and finally the magnetic particles 10 enter the detection buffer 114 which allows them to bind to the surface 20 of the IC 16.

Although the description above contains many details, these should not be construed as limiting the scope of the disclosure but as merely providing illustrations of a variety of variations of the disclosed device and method. Therefore, it will be appreciated that the scope of the disclosure herein fully encompasses other variations which may become obvious to those skilled in the art. References to an element in the singular is not intended to mean "one and only one" unless explicitly so stated, but rather "one or more." The terms device and system are used interchangeably herein. Devices, systems, elements, features, characteristics, steps, and methods disclosed herein can be used in any functional combination beyond those shown, and are only shown in the combinations explicitly illustrated for exemplary purposes. All structural, chemical, and functional equivalents to the elements of the above-described disclosure that are known to those of ordinary skill in the art are expressly incorporated herein by reference and are intended to be encompassed by the present claims.

What is claimed is:

1. A device for analyzing a biological fluid sample comprising:
   a filter configured to filter the biological fluid sample resulting in a filtrate comprising a target analyte;
   an exposed surface having a sensor area, wherein the sensor area comprises a sensor coated with a chemical specific for the target analyte;
   a sedimentation capillary disposed above the sensor area having an outlet in proximity to the sensor area;
   a dried reagent at the top of the sedimentation capillary, wherein the reagent comprises magnetic particles functionalized to react with the target analyte;
   a delivery capillary having an inlet in proximity to the filter and an outlet fluidically connected to the sedimentation capillary, wherein the delivery capillary is configured to deliver the filtrate to the sensor area before the filtrate flows up the sedimentation capillary to the dried reagent; and
   a bulking agent, wherein the bulking agent is configured to dry the magnetic particles, and wherein the bulking agent is configured to solubilize upon contact with the filtrate.

2. The device of claim 1, wherein the magnetic particles can sediment through the sedimentation capillary to the exposed surface upon contact with the filtrate.

3. The device of claim 1, wherein the sensor is configured to detect magnetic particles that specifically bind to the sensor area.

4. The device of claim 1, wherein the sensor comprises an optical sensor.

5. The device of claim 1, wherein the sensor comprises a magnetic sensor.

6. The device of claim 1, wherein the biological fluid sample comprises whole blood, and wherein the filter is further configured to block blood cells in the whole blood.

\* \* \* \* \*